US011965872B2

United States Patent
Krueger et al.

(10) Patent No.: US 11,965,872 B2
(45) Date of Patent: Apr. 23, 2024

(54) HIGH PRESSURE CORE CHAMBER AND EXPERIMENTAL VESSEL

(71) Applicant: CONOCOPHILLIPS COMPANY, Houston, TX (US)

(72) Inventors: Martin C. Krueger, Houston, TX (US); Shaina A. Kelly, Houston, TX (US); Gerald E. Michael, Houston, TX (US); Thiago B. Simoes Correa, Houston, TX (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 101 days.

(21) Appl. No.: 17/348,883

(22) Filed: Jun. 16, 2021

(65) Prior Publication Data

US 2021/0389294 A1  Dec. 16, 2021

Related U.S. Application Data

(60) Provisional application No. 63/039,723, filed on Jun. 16, 2020.

(51) Int. Cl.
*G01N 33/24* (2006.01)
*E21B 49/08* (2006.01)
*G01N 15/08* (2006.01)

(52) U.S. Cl.
CPC ......... *G01N 33/24* (2013.01); *E21B 49/0875* (2020.05); *G01N 15/08* (2013.01)

(58) Field of Classification Search
CPC ..... G01N 33/24; G01N 15/08; E21B 49/0875
See application file for complete search history.

(56) References Cited

U.S. PATENT DOCUMENTS

| | | | |
|---|---|---|---|
| 3,986,555 | A | 10/1976 | Roberstson |
| 4,230,192 | A | 10/1980 | Pfannkuche |
| 4,256,192 | A | 3/1981 | Aumann |
| 4,258,803 | A | 3/1981 | Thompson et al. |
| 4,573,342 | A | 3/1986 | Jones |
| 4,649,737 | A | 3/1987 | Jones |
| 4,702,168 | A | 10/1987 | Colle et al. |

(Continued)

FOREIGN PATENT DOCUMENTS

| | | |
|---|---|---|
| GB | 2184835 A | 7/1987 |
| GB | 2293653 A | 4/1996 |

(Continued)

OTHER PUBLICATIONS

Kenyon, W.E. Petrophysical Principles of Applications of NMR Logging. The Log Analyst (2009) 38 (2): 21-43.

(Continued)

*Primary Examiner* — Michael J Dalbo
*Assistant Examiner* — Kaleria Knox
(74) *Attorney, Agent, or Firm* — Boulware & Valoir PLLC

(57) ABSTRACT

A high pressure core chamber for use in collecting pressurized core samples from a reservoir is equipped with at least two high pressure access valves, allowing the core chamber to also function as a vessel for various high pressure experiments. In some embodiments, the core chamber is also equipped with a heater, allowing high pressure, high temperature experiments, and thus duplicating reservoir conditions. Various assays using the core chamber are also described.

10 Claims, 12 Drawing Sheets

(56) References Cited

U.S. PATENT DOCUMENTS

| | | |
|---|---|---|
| 4,950,844 A | 8/1990 | Hallmark |
| 5,193,059 A | 3/1993 | Tiab et al. |
| 5,263,360 A | 11/1993 | Blauch et al. |
| 5,265,462 A | 11/1993 | Blauch et al. |
| 5,297,420 A | 3/1994 | Gilliland et al. |
| 5,359,194 A | 10/1994 | Moss |
| 5,741,959 A | 4/1998 | Garcia et al. |
| 7,347,284 B2 | 3/2008 | Arian et al. |
| 7,600,580 B2 | 12/2009 | Caravatte et al. |
| 8,122,976 B2 | 2/2012 | Bartelle et al. |
| 8,256,282 B2 | 9/2012 | Schlachter |
| 8,230,946 B2 | 11/2012 | Crawford et al. |
| 8,307,704 B2 | 11/2012 | Georgi et al. |
| 8,356,510 B2 | 1/2013 | Coenen |
| 8,453,766 B2 | 6/2013 | Graterol et al. |
| 8,621,920 B2 | 1/2014 | Reid et al. |
| 9,051,804 B2 | 6/2015 | Reid et al. |
| 9,243,466 B2 | 1/2016 | Klomp |
| 9,291,541 B2 | 3/2016 | Kim et al. |
| 9,376,879 B2 | 6/2016 | Mizuguchi |
| 9,506,307 B2 | 11/2016 | Kinsella |
| 9,745,811 B2 | 8/2017 | Wesemeier et al. |
| 9,828,820 B2 | 11/2017 | Gupta et al. |
| 9,874,063 B2 | 1/2018 | Arian et al. |
| 9,926,756 B2 | 3/2018 | Wesemeier et al. |
| 9,951,574 B2 | 4/2018 | Westacott et al. |
| 10,047,580 B2 | 8/2018 | Morgan et al. |
| 10,174,613 B2 | 1/2019 | Quintero et al. |
| 10,221,684 B2 | 3/2019 | Westacott et al. |
| 10,260,300 B2 | 4/2019 | Dorovsky et al. |
| 10,301,936 B2 | 5/2019 | Westacott et al. |
| 10,317,351 B2 | 6/2019 | Chong et al. |
| 10,550,655 B2 | 2/2020 | Jones et al. |
| 10,761,157 B2 | 9/2020 | Chen et al. |
| 11,187,691 B2 * | 11/2021 | Zhu .......................... E21B 43/01 |
| 2014/0090835 A1 | 4/2014 | Griffin |
| 2015/0354352 A1 * | 12/2015 | Ezzat .................... G01N 33/24 |
| | | 73/152.05 |
| 2018/0044572 A1 * | 2/2018 | Danican ................ C09K 8/602 |
| 2018/0148988 A1 | 5/2018 | Dusterhoft et al. |
| 2018/0217073 A1 * | 8/2018 | Chen .................... G01R 33/307 |
| 2018/0298709 A1 * | 10/2018 | Gupta ....................... G01V 5/04 |
| 2018/0371904 A1 | 12/2018 | Zuilekom et al. |
| 2021/0018411 A1 * | 1/2021 | Manning ................. G01N 3/10 |

FOREIGN PATENT DOCUMENTS

| | | | |
|---|---|---|---|
| WO | 2019070252 A1 | 4/2019 | |
| WO | 2019090316 A1 | 5/2019 | |
| WO | WO-2019090316 A1 * | 5/2019 | ............... G01V 3/32 |

OTHER PUBLICATIONS

Murphy, D.P. 1995. NMR logging and core analysis—simplified. World Oil (1995) 216 (4): 65-70. OSTI ID 39931.

Woessner, D.E. The early days of NMR in the Southwest. Concepts in Magnetic Resonance (2001)13 (2): 77-102.

Zhao, T.; Verma S.; Devegowda, D.; Jayaram, V. TOC Estimation in the Barnett Shale From Triple Combo Logs Using Support Vector Machine. SEG Annual Meeting, 2015, Paper #SEG-2015-5922788.

Truax J.; Galford, J.; Moake, G.; Torres, D.; Cherry, R.; Mandal, B.; Mishra, A.; Martin, S. L.; Quintero, A. Performance of a new 2.35-in. wireline or memory quad combo for through-bit or small-hole logging. SPE Annual Technical Conference and Exhibition. 2011, Paper #SPE-147400-MS.

Clark, A. J. (2009). Determination of recovery factor in the Bakken formation, Mountrail County, ND. SPE Annual Technical Conference and Exhibition. 2009, Paper #SPE-133719-STU.

Alhashim, H. W.; Zhang, F.; Schechter, D. S.; Chen J-H. Investigation of the effect of pore size distribution on the produced oil from surfactant-assisted spontaneous imbibition in ULRs. SPE Annual Technical Conference and Exhibition. SPE-195931-MS.

Dunn, K.-J.; Bergman, D.J.; Latorraca, G.A. Nuclear Magnetic Resonance Petrophysical and Logging Applications. (2002) vol. 32, New York: Handbook of Geophysical Exploration: Seismic Exploration, Pergamon Press.

* cited by examiner

HIGH PRESSURE CORE CHAMBER AND EXPERIMENTAL VESSEL

PRIOR RELATED APPLICATIONS

This application claims priority to U.S. Ser. No. 63/039,723, filed Jun. 16, 2020, and incorporated by reference in its entirety for all purposes.

FIELD OF THE DISCLOSURE

This disclosure provides a new core drilling and fluid preservation tool for drilling core samples, that can also be used as an experimental vessel for bench top experiments. This new vessel allows more accurate determination of various core properties than heretofore possible.

BACKGROUND OF THE DISCLOSURE

One of the ways of studying rock characteristics is to drill and analyze a core sample from a reservoir. Similar to a drill bit, the rotary coring bit consists of solid metal with diamonds or tungsten for cutting at the reservoir rock; but unlike a drill bit, a rotary coring bit has a hollow center. The cutting apparatus thus surrounds the hollow center, called the core barrel, where the core sample is stored. The core barrel is made up of an inner and outer barrel separated by ball bearings, which allows the inner barrel to remain stationary and retain the core sample, while the outer barrel is rotated by the drill string and cuts the core. The core catcher is located within the core barrel. The core catcher has finger-like apparatuses that move the core sample farther into the barrel and keep it from falling back into the well. After the core sample has been cut from the well, the drill string is raised, and the rotary coring bit, barrel and catcher are removed, and the core sample is retrieved. The drill bit is reattached, and drilling can commence again.

However, obtaining an unaltered core sample from a reservoir with these prior art devices remains challenging. As the core is retrieved from deep in the reservoir, the temperature and pressure decreases. Pressure reduction allows gases to evolve out of solution and together with free gases, expand, resulting in reservoir fluids being forced out of the core. Thus, accurate sampling, especially of fluids, is difficult, if not impossible to obtain.

To address this problem, the core samples are sometimes collected and sealed in a chamber, in a method known as "pressure coring". Pressure coring at least partially solves the problem by maintaining the core specimen at bottom-hole pressure—BHP—until the core fluids can be immobilized. This concept, first proposed by Sewell in the 1930's, remained a "laboratory" tool until the late 1970's, but with the advent of ever improving technology, the method is much more popular now.

However, the samples are pressurized only until reaching the surface, and many laboratory analyses are still performed at room temperature and atmospheric pressure. Thus, the samples still are subject to change as a result of the changed environment, and therefore the data is not fully representative of reservoir conditions.

This disclosure addresses this issue and further develops core drilling technology to further optimize bench top testing of core samples.

SUMMARY OF THE DISCLOSURE

The disclosure provides a new high pressure ("HP") core chamber or a complete coring system including same and methods of use. The novel core chamber is used with a coring tool to cut core samples and to house those samples under reservoir conditions in sealed, pressurized containers with at least two valves allowing for use of the core chamber as an experimental vessel as well as for delivery of the core to the surface.

Currently, sealed cell technology (one example is known as "CoreVault®") takes a sample in an inert high-density fluid (i.e. FC40). Once the sample is returned to the surface, the pressure is measured, the released gases are measured, and temperature is decreased to measure compressibility. The sample is then removed from the sealed cell and core samples are tested at atmospheric pressure. It would be more representative of reservoir conditions, however, to test samples at reservoir conditions, before any changes caused by the changing environment could occur. However, there is currently no mechanism to test core samples and the fluids therein at reservoir temperatures and pressures.

This disclosure adds first and second access ports to a sealed HP core chamber, which allows a battery of tests to be conducted at reservoir pressure (and in some embodiments temperature) that are currently conducted at atmospheric pressure. In some embodiments, the fluid is assayed as it emerges (or shortly thereafter) from the second access point.

In addition, by replacing the inert, high density fluid with water, hydrocarbon, or other treatment fluid, the reservoir cores can be tested at reservoir pressure (P) or pressure and temperature (PT) with different fluids. Ideally, there would be an inlet valve at one end and an exit valve at the opposite end, this would allow one fluid to displace the other rapidly and evenly, allowing a variety of tests that heretofore have not been possible. However, this configuration is not essential, and ports may be placed at varying locations. In some embodiments, a second vessel is connected to the primary core chamber in order that test fluids ca be brought to reservoir PT before introduction into the test core chamber.

The tests that can be conducted at reservoir temperature/pressure include core sample chemistry, imbibition, wettability, acid/pH treatment, salinity, fluid/rock interphase, and the like. In one embodiment, the operator can test one reservoir fluid, recharge with hydrocarbon, test another reservoir fluid, etc. This would require a uniform sample with uniform displacement, hence the preference for opposing ports.

The inventive core chamber/vessel can be used to measure or observe the fluid-rock and fluid-fluid interactions, especially imbibition (adsorption or absorption) and wettability. A range of fluids can be tested, ranging from fresh water to gel filtrate (broken gel completion fluid) with any combination of varying salinities, varying pH, varying chemical additives (surfactants, solvents, dispersants, etc.), and varying miscible or dissolved gases.

The core is not cleaned in the conventional sense (at least initially—it may be extracted once reservoir PT tests are complete) because these cores collected in a sealed cell, in a stable borehole environment (no chemical or physical invasion, no production), and surrounded by an inert high-density fluid. Thus, the native environment is largely preserved.

It is also possible that porosity and permeability may be extrapolated from the time-pressure relationship during drawdown and blowdown. Utilizing the pressure-volume-temperature (PVT) relationship, we may be able to discern porosity and permeability characteristics as gas travels out of the rock matrix and into the free space within the sealed vessel. Similar to a gas transient model (GTM) where pressure is applied to a sample and pressure fall of is observed as gas reconstitutes within pore space.

Porosity and saturations can be measured during multiple time lapse NMR measurements using low-field, bench-top pulse-NMR spectrometers developed similar to logging tools so that wellbore measurements could be duplicated on core samples in the laboratory. Low-field NMR operate and record data in the same manner as NMR-logging tools in a nondestructive manner. NMR and conventional capillary-pressure measurements can be performed on the same samples, in both the saturated and partially saturated states. Low-field spectrometers provide the ability to make repeatable measurements of rock- and fluid-NMR properties. This ability, in turn, permits correlation and calibration of laboratory and field measurements and also permits direct transfer of interpretation models developed in the laboratory to logging data. Low-field NMR also provided correlation and calibration of petrophysical measurements on drill cuttings.

Laboratory NMR studies are routinely conducted for the following purposes:
Verifying formation porosity
Evaluating textural effects, such as microporosity, on NMR-log response
Determining formation-specific models that enhance the accuracy of determining bulk-volume-irreducible (BVI) water, free-fluid index (FFI), and, ultimately, permeability
Developing models to identify and quantify hydrocarbons, including residual oil
Developing models to predict changes in pore size (facies)
See for example Kenyon (1997); Murphy (1995); Woessner (2001); and Dunn et al. (2002) at petrowiki.org/NMR_petrophysics.

All of these tests would lead to improved reservoir treatments, testing of reservoir treatments before delivery, and improved or enhanced oil recovery.

---

The invention includes any one or more of the following embodiments, any one or more of which can be combined with any other one or more in any combination(s) thereof.

1. A method of determining assaying a reservoir core sample at reservoir pressure and temperature (RPT), said method comprising:
a) collecting a core sample from a reservoir in a high pressure chamber operably equipped with a pressure sensor, a temperature sensor, a heater, a first high pressure access port at a first end and a second high pressure access port at a second end, said core sample in an inert fluid at reservoir PT;
b) injecting a first test fluid into said first access port and collecting egressed inert fluid at said second access port without exposing said high pressure chamber to ambient pressure or temperature (APT);
c) injecting a second test fluid into said first access port and collecting egressed first test fluid at said second access port without exposing said high pressure chamber to APT;
d) measuring a first characteristic of said egressed first test fluid and/or said egressed first inert fluid;
e) determining a second characteristic of said reservoir core sample from said first characteristic.
Any method herein described, further comprising repeating steps b-e with one or more additional test fluids.
Any method herein described, wherein injecting step c occurs after said first test fluid has reach an equilibrium.
Any method herein described, wherein injecting step c occurs at timed intervals or continuously.
Any method herein described, wherein pressure is monitored throughout the method.
Any method herein described, wherein said first or second test fluid is a brine.
Any method herein described, wherein said first or second test fluid is a stimulation fluid.
Any method herein described, further comprising a subsequent step of removing said core sample from said high pressure core chamber and assaying one or more characteristics of said core sample.
Any method herein described, wherein said first characteristic is volume of oil produced, volume of gas produced, volume of water produced, chemical content of oil, chemical content of gas, NMR of oil, water or gas produced, and the like.
Any method herein described, wherein said second characteristic is microporosity, bulk-volume-irreducible (BVI) water, free-fluid index (FFI), permeability, residual oil, pore size (facies), wettability, pore volume compressibility, relative permeability, electrical properties, geological testing, compositional analysis, sedimentology, fluid saturation, porosity, permeability, or combinations thereof.
A method of determining wettability of a core sample, said method comprising:
a) collecting a core sample from a reservoir in a high pressure chamber operably equipped with a pressure sensor, a temperature sensor, a heater, a first high pressure access port at a first end and a second high pressure access port ata second end, said core sample in an inert fluid at reservoir pressure and temperature;
b) injecting a first test fluid into said first access port and collecting said inert fluid at said second access port without exposing said high pressure chamber to ambient pressure or temperature;
c) measuring a first change in pressure within the chamber over time; and
d) determining wettability from a measured change in pressure.
Any method herein described, further comprising repeating steps b-d with one or more additional test fluids.
Any method herein described, wherein said core sample is recharged with oil before a subsequent test fluid is added.
Any method herein described, wherein step c measuring occurs after pressure has reach an equilibrium.
Any method herein described, wherein said first test fluid is a brine.
Any method herein described, wherein said first test fluid is a stimulation fluid.
Any method herein described, comprising injecting a second test fluid into said access port without exposing said high pressure chamber to ambient pressure or temperature and collecting said first test fluid at said second access port and measuring a second change in pressure within the chamber over time.
Any method herein described, wherein said second test fluid is a stimulation fluid.
Any method herein described, further comprising a subsequent step of removing said core sample from said high pressure core chamber and assaying one or more characteristics of said core sample.

| | |
|---|---|
| The invention includes any one or more of the following embodiments, any one or more of which can be combined with any other one or more in any combination(s) thereof. | |
| Any method herein described, comprising a subsequent step of removing said core sample from said high pressure core chamber and measuring low-field NMR of said core sample. Any method herein described, further comprising a subsequent step of measuring low-field NMR of said core sample and/or any fluids egressing from said core sample. | |

As used herein, "high pressure" means higher than 1 atm, and includes all typical downhole pressures (e.g. up to and even beyond 25,000 psi).

As used herein, a "high temperature" means any temperature greater than 100° F., typically about 200-400° F.

As used herein, "reservoir PT" or "reservoir P" or "reservoir T" refer to reservoir pressure and temperature conditions at the depth the oil is found at. If the depth of the play is significant, any relevant PT within the play can be used. For example, when testing cores from 2,5000 feet deep, one would select the PT at that depth. For plays of less depth, the average PT may suffice.

The use of the word "a" or "an" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

Any claim or claim element introduced with the open transition term "comprising," may also be narrowed to use the phrases "consisting essentially of" or "consisting of," and vice versa. However, the entirety of claim language is not repeated verbatim in the interest of brevity herein.

The following abbreviations may be used herein:

| ABBREVIATION | TERM |
|---|---|
| API | American Petroleum Institute |
| BVH | bulk volume hydrocarbon |
| CT | computerized tomography |
| Dual Energy CT | dual energy CT |
| FC40 | a commercial inert fluid used to store cores |
| GTM | gas transient model |
| HP | high pressure |
| IOR | Improved Oil Recovery |
| LWD | logging while drilling |
| MWD | measurement while drilling |
| NMR | nuclear magnetic resonance |
| P | pressure |
| PT | pressure & temperature |
| Quad Combo | standard logging combo: GR, resistivity, density/neutron, sonic |

-continued

| ABBREVIATION | TERM |
|---|---|
| RFPX | a Halliburton trademark |
| RSW | rotary side wall (side wall core) |
| SEM | scanning electron microscopy |
| SOP | standard operating procedure |
| T | Temperature |
| ~ | about |

BRIEF DESCRIPTION OF THE DRAWINGS

FIG. 2A shows the tool downhole in the well, and FIG. 2B-D shows the core bit (FIG. 2B) rotating into position (FIG. 2C) and obtaining a core sample (FIG. 2D).

FIG. 5A shows a single split port with and in- and out-flow lines or channels with a threaded fit to a bleed valve in FIG. 5B.

FIG. 5C shows an sealed high pressure chamber with two ports on its cap. An existing unit can easily be reconfigured this way by changing out the cap.

FIG. 5D shows a newly designed chamber with one port on the upper cap and one port on chamber base (FIG. 5D) or lower cap (FIG. 3A).

DETAILED DESCRIPTION OF THE DISCLOSURE

The disclosure provides a high pressure core chamber having at least two high pressure access ports so that the chamber can be used for both core retrieval and for subsequent experimentation at high pressure. The core chamber thus serves both delivery and experimental vessel functions, though samples of the fluids are removed for the later analysis. Samples can be removed and assayed at timed intervals or continuously, or the fluids can be equilibrated and then sampled for analysis.

Figure 1:
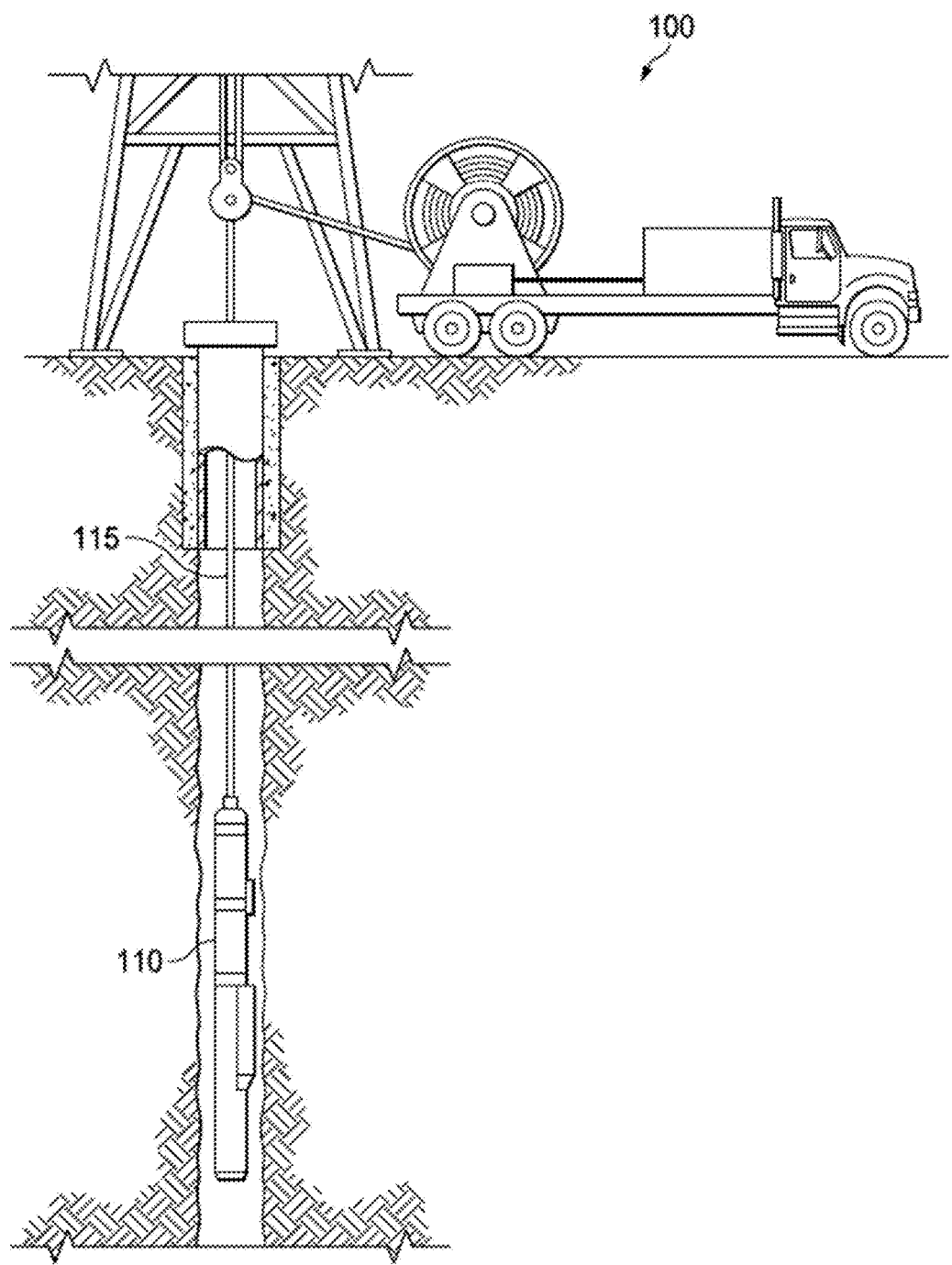
FIG. 1 is an example wireline implementation of a coring tool system.

FIG. 1 shows an example system 100 of the present disclosure. In the example shown, tool 110 is placed in a wellbore by wireline 115. In other embodiments, tool 110 is placed in wellbore by wired coil tubing. In yet other embodiments, tool 110 is placed in the borehole as part of a measurement while drilling (MWD) portion of a drill string or as part of a logging while drilling (LWD) portion of a drill string. In other implementations, the tool 110 may be on a drillpipe as part of a wired drillpipe system.

Figure 2A:
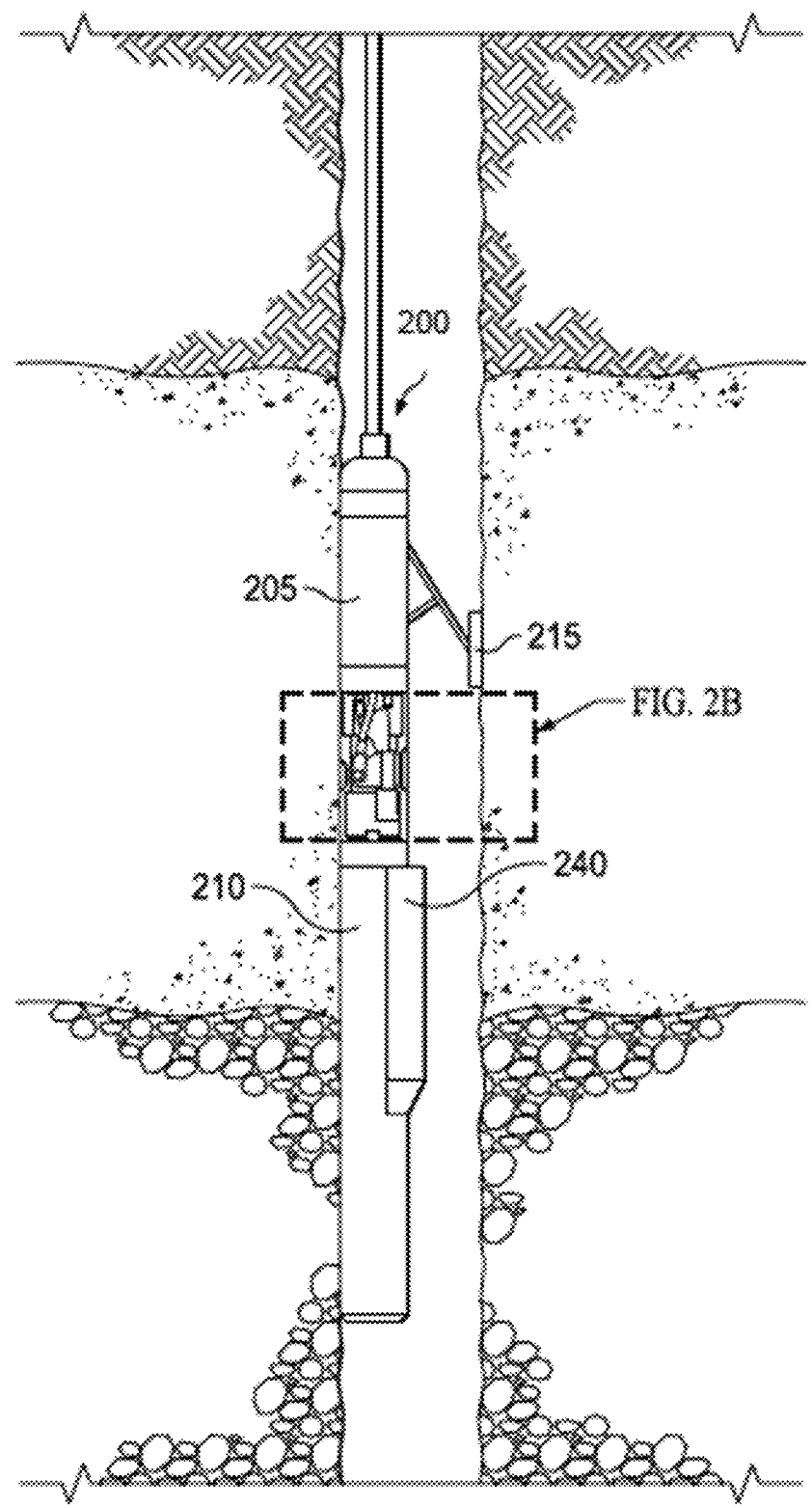
FIG. 2A-D is an example implementation of the system in a downhole location.

FIG. 2A shows an exemplary tool 200 that has been lowered to a depth of interest. The example tool 200 includes a sidewall drilling tool 205 and a high pressure (HP) core chamber 210. Once the tool 200 is in a region of interest the sidewall drilling tool 205 extends a stabilizing pad 215 against the wall of the borehole and rotates the core drilling bit 217 to face the wellbore wall.

Figure 2B:
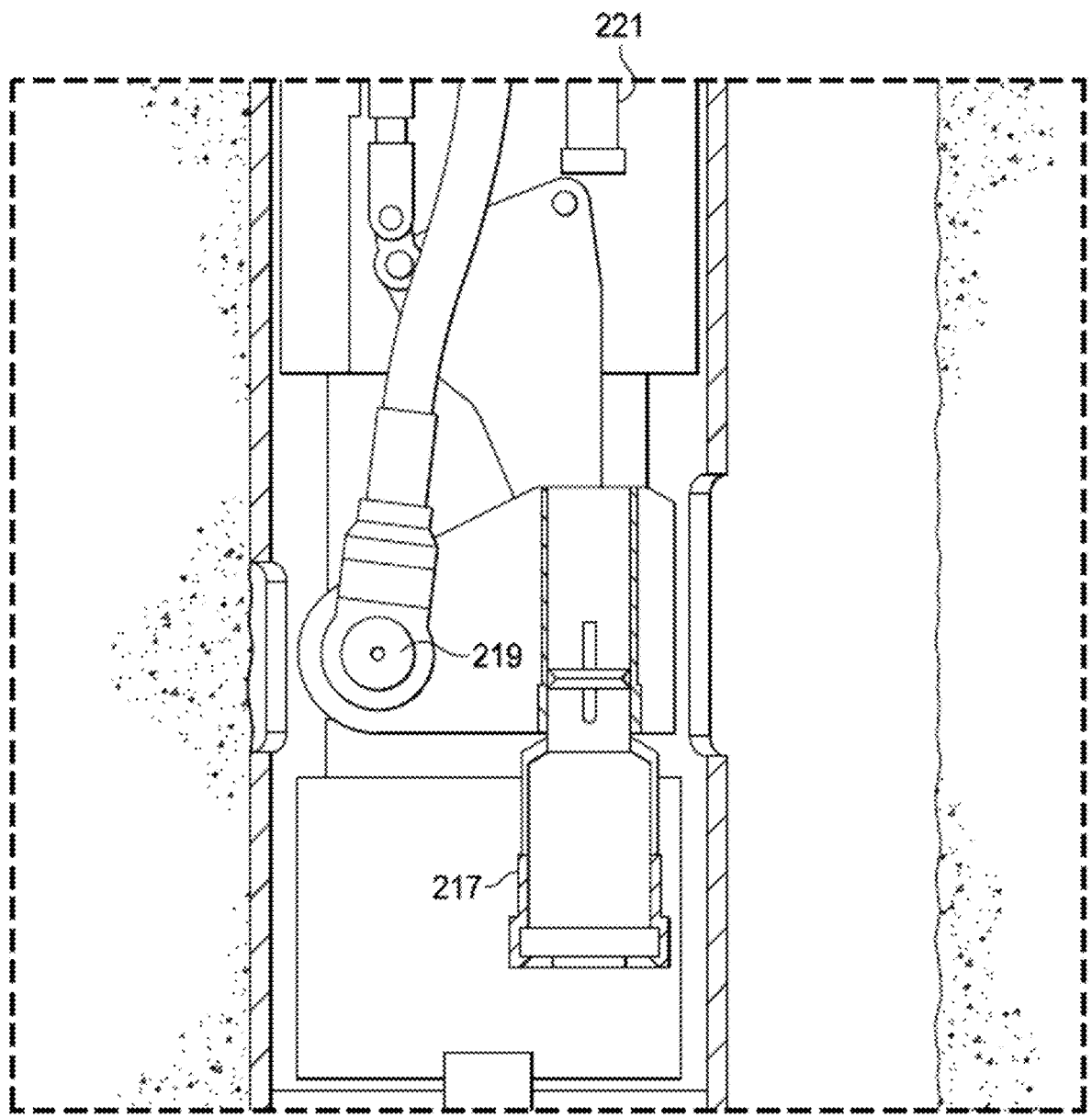
Figure 2C:
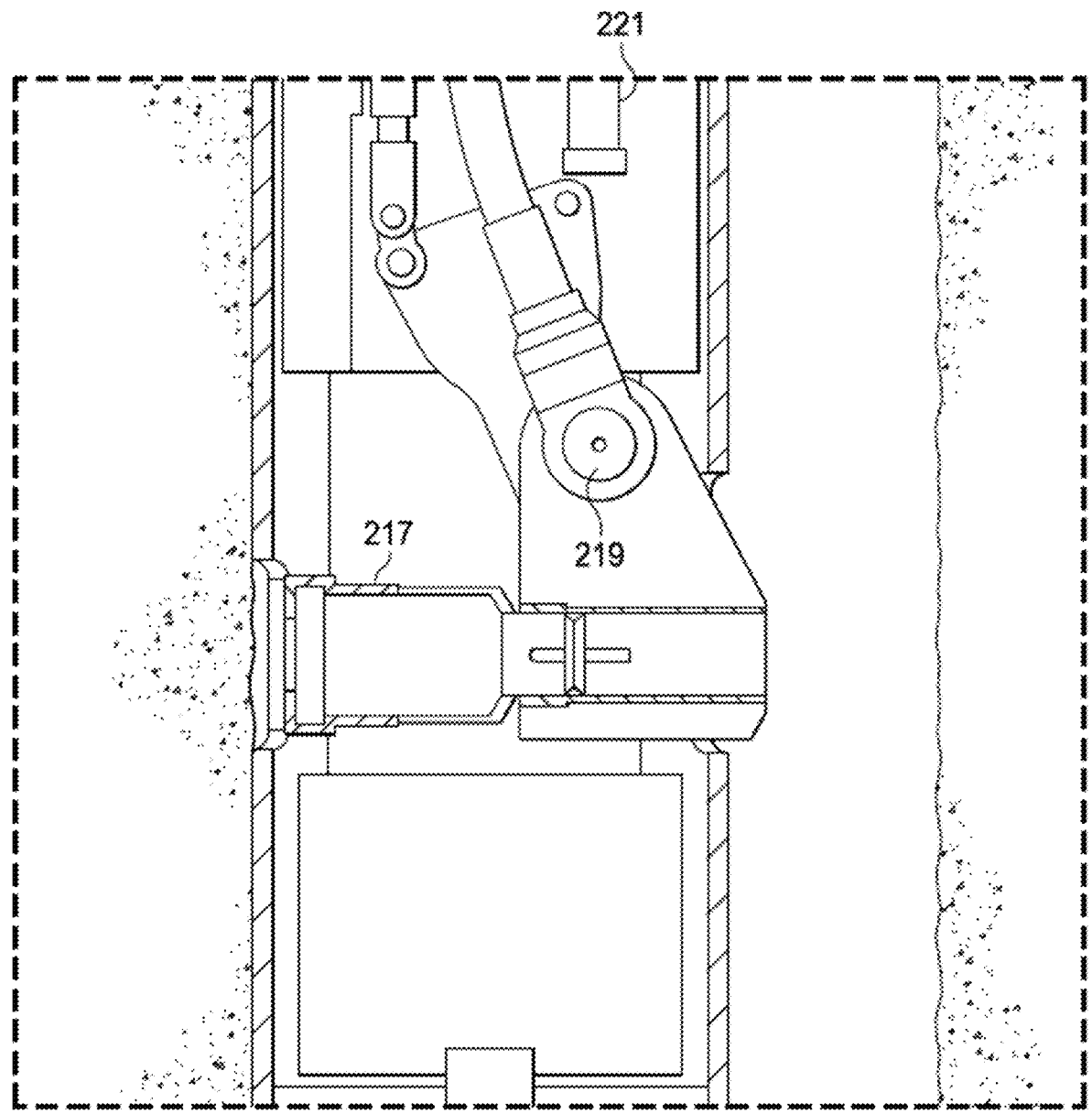
Figure 2D:
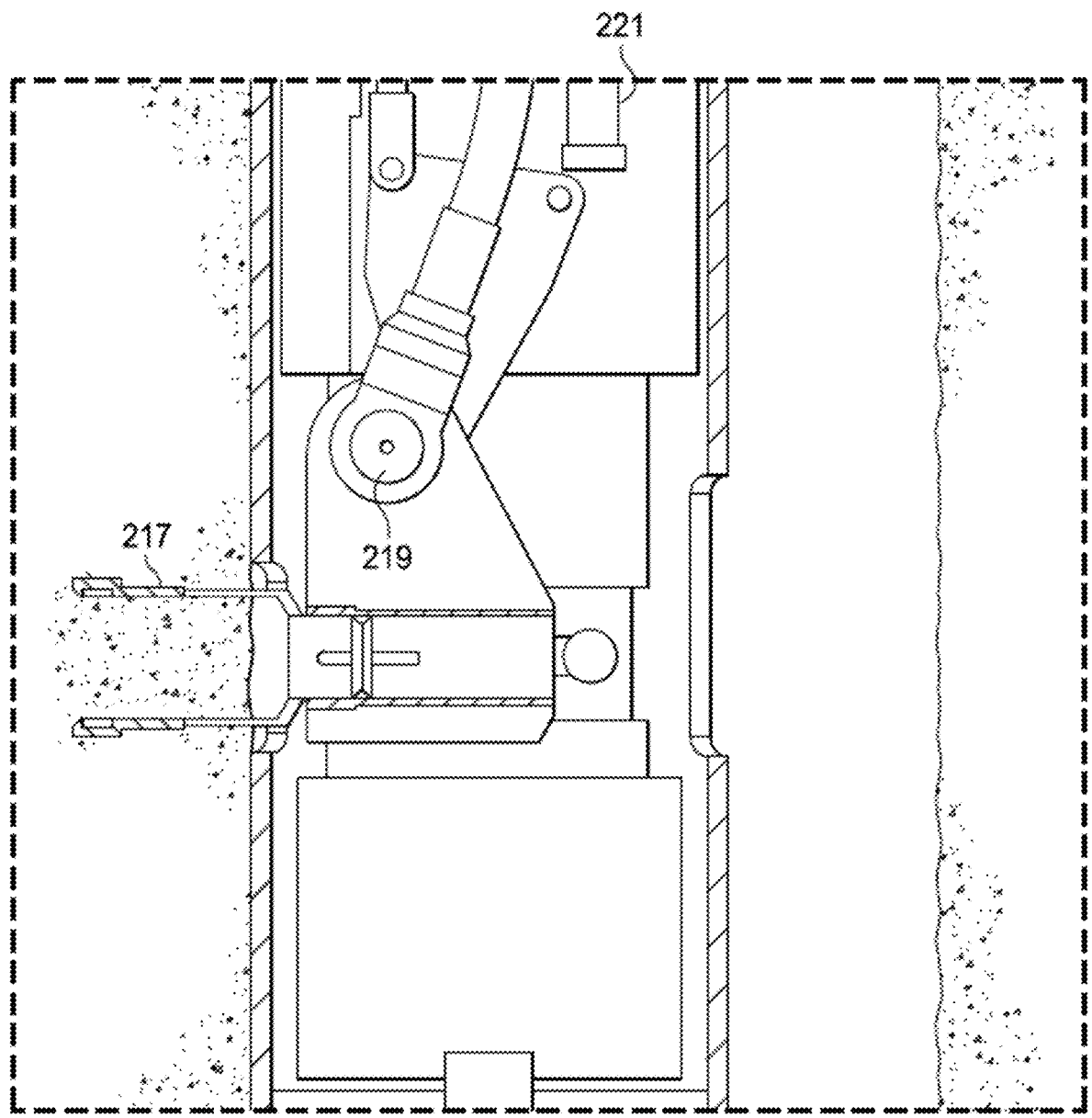

In FIG. 2B-D a bell crank 219 allows the coring bit to be both rotated and moved from an orientation parallel to the tool and wall (2A) to a perpendicular orientation (2B) and then rotated to cut into the reservoir wall (2D). Once drilled, a sharp lateral translation of the tool breaks the core sample free from the formation wall, and the coring bit 217 is retracted back into the tool, again rotated parallel to the tool and the core pushed into the core chamber by, for example, a plunger 221. When all core samples are collected, a cover activation mechanism 240 closes the core chamber, sealing in the pressure. See e.g. US2014367086 (incorporated by reference in its entirety for all purposes) for additional details of an exemplary sidewall coring tool and cover activation mechanism 240.

Figure 3A:
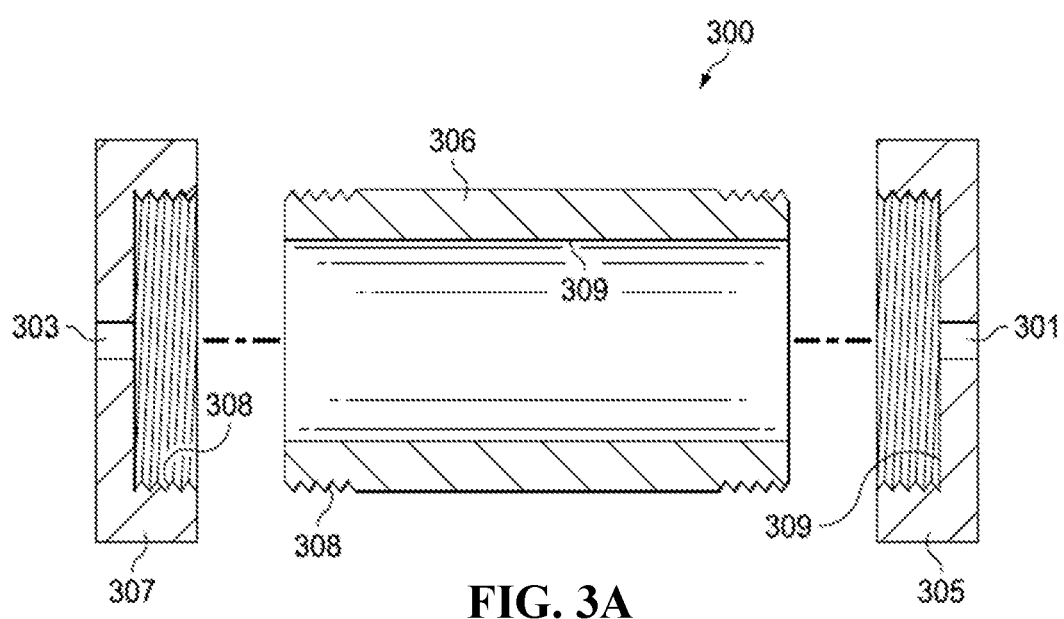
FIG. 3A is a cut away section of a simple HP core chamber that has at least two ports for sample access.

FIG. 3A is a cross section of a simple schematic of an HP core chamber 300 that has at least two ports 301, 303 for sample access. The core chamber 300 itself is generally a hollow cylinder, and made of any material suitable for a high pressure container. Typically, the core chamber will be metal, such as stainless steel 306, possibly with passivated or inert coating on its inner surface 309. Core chamber 300 has an upper end that is closable via upper cover 305, and lower end that can be a blind end or reversibly covered (assuming the core feed in the top), as desired, but is preferably covered with lower cover 307. In other embodiments, where the core feeds in from the bottom, it can be the top end that is blind or reversibly covered. Preferably both ends have a reversible cover. In this instance, both covers 305 and 307 are threaded 308 covers, but any means of ensuring a pressurized seal can be used.

Access ports 301, 303 can be at any location, but are preferably at the upper and lower ends, and even more preferred in covers 305, 307. This placement allows the ingress of a fluid at one end and its egress at the other, thus passing each core sample, and is the most convenient for subsequent core experiments using the high pressure core chamber.

Access ports are designed to withstand high pressures, but still allow access when desired, and can be provided by any means known in the art, including the HP™ and MH™ high pressure access ports by Metex (Toronto, ONT), the Habonim (Israel) high pressure valve series, the High Pressure Access Systems by Metal Samples (Munford AL), High Pressure products by High Pressure Equipment (Erie PA) or a port may be machined dependent upon needs and sizes.

Figure 3B:
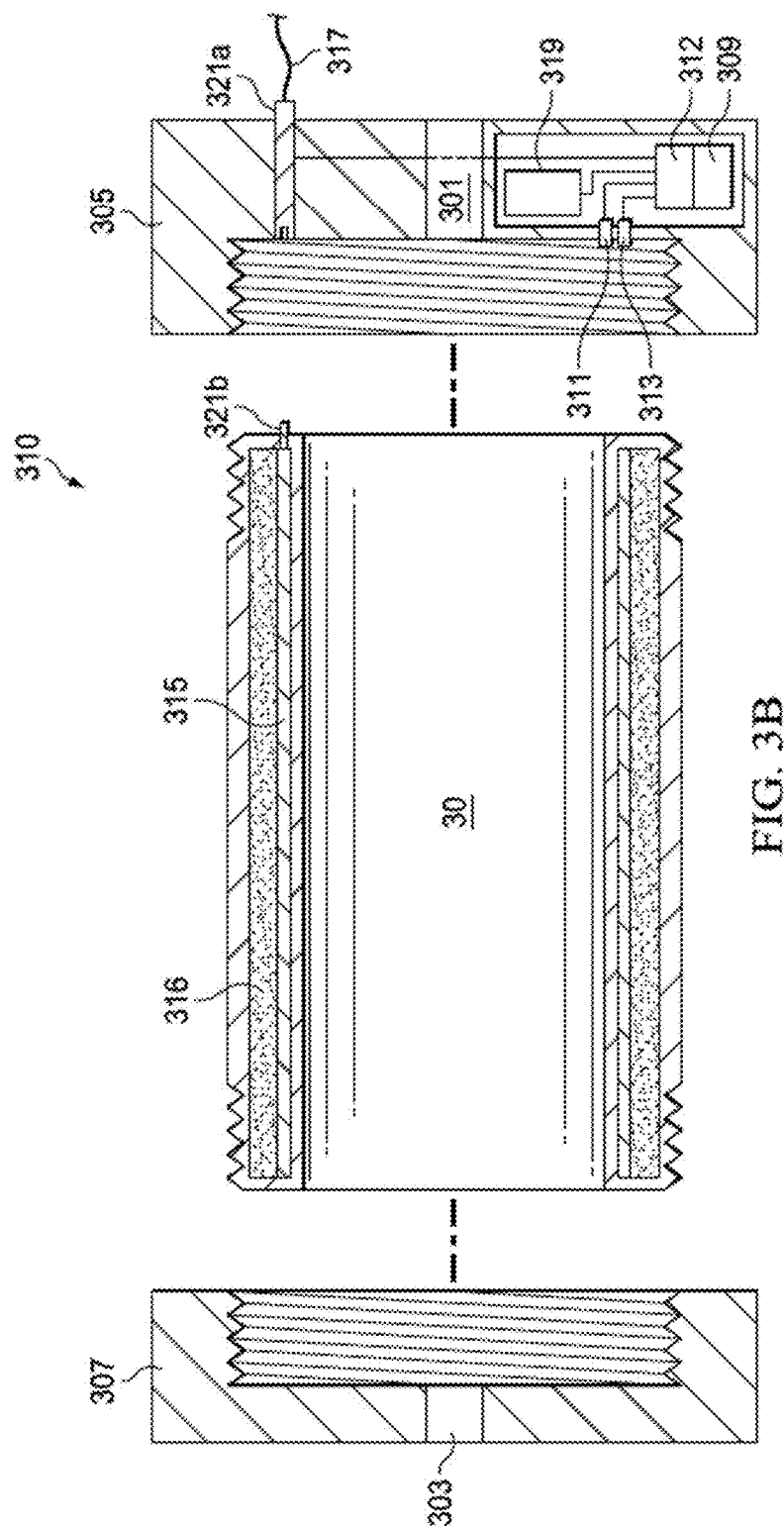
FIG. 3B shows a more sophisticated model with a controller, sensors, and heater.

In a preferred embodiment shown in FIG. 3B, the core chamber 310 is equipped with operably connected electronic parts, including one or more of a controller 309, temperature sensor 311, pressure sensor 313, and processor 312, which can function to obtain PT readings and/or act on same, e.g., by reporting PT readings to the surface and/or by maintaining the temperature via heater 315. However, sensors and controller may also be outside of the core chamber, in the corer tool itself, especially where heater 315 is omitted. Heater 315 could also be a heater/cooler (e.g., a Peltier as shown), thus allowing the freezing of samples if desired.

Preferably, the core chamber has an inner chamber 30 that is insulated with insulating material 316. This better allows the core to be maintained at reservoir temperatures for subsequent analysis. The heater can be supported by either wireline 317 or internal batteries 319. Batteries will allow the core chamber to be removed and kept at temperature for a longer period of time, but in those instances where local lab facilities are available, or a heated container is used to keep a sufficiently well-insulated core chamber warm on removal from the corer tool, providing power downhole via wireline may suffice. It may also be advantageous to provide both options to the user.

Wireline 317 can also provide control signals to the controller 309 via electrical connector 321, which can be a single connector if all electrical parts are in the same location, or can be in multiple parts (321a, 321b) if, as shown, the Peltier heater 315 surrounds the inner chamber 30, while the controller is in the upper cover 305. Likewise, the same wireline can transmit signals, e.g., temperature and pressure readings, back to the surface. In the alternative or in addition, the data can be stored in processor 312 and accessed at the surface.

The core chamber can be a stand-alone device, sized to fit with any existing available coring device, but in one embodiment is sized and shaped to operably connect with Halliburton's Xaminer® Coring Tool system. This sidewall corer allows the lateral coring of as many as 10 samples in an hour, and storage of all 10 inside the core chamber at the same high pressure encountered down hole. It thus allows sampling of several locations within a given interval and will provide an average of reservoir characteristics over that interval.

The core chamber could also be used with other core systems, including The RockStrong® coring system by Halliburton, the Hilti DD by Hilti, the Mechanical Sidewall Coring Tool by Schlumberger, and the like. However, a complete new system can be designed as well. In such case, the invention may comprise all or any part of the complete system as long as the dual access core chamber is included therein.

Figure 4:
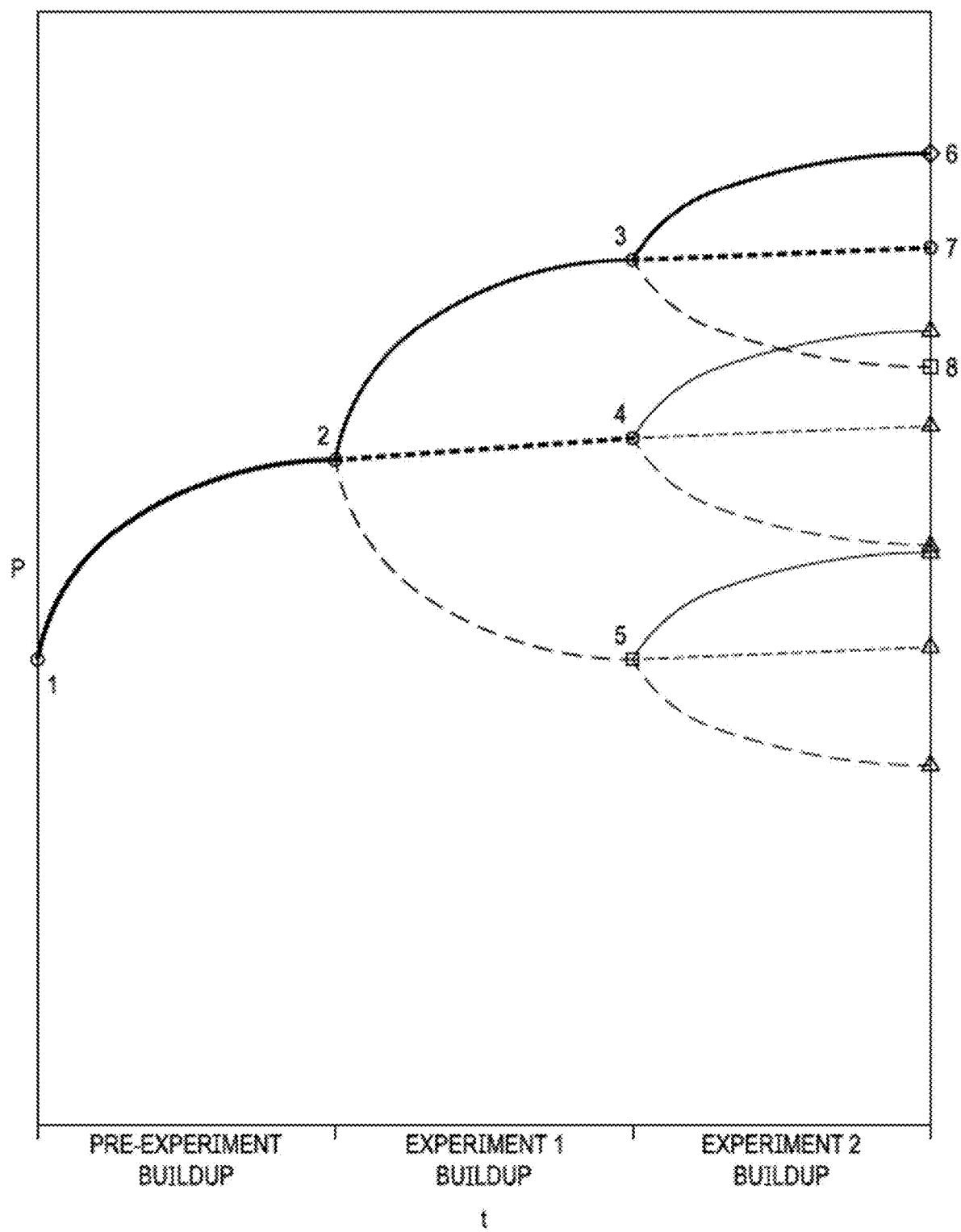
FIG. 4 is a graph of change in pressure (ΔP) versus time (t depending upon porosity and flow in the sample). Once equilibrium is reached, additional fluid could be added to see if the limiting factor is the core sample or the fluid. Different fluids may be tested to see if one elucidates more hydrocarbon release.

FIG. 4 presents a simple schematic of one exemplary assay of the invention, wherein at point 1, the sealed chamber is connected to an external pressure regulatory system and equilibrium of the closed system is reached. Ideally, the temperature of the core samples would be the same as reservoir temperature, which can be preferably done by using a temperature regulated high pressure chamber, or by bringing a sealed high pressure chamber that lacks temperature control back to reservoir temperature as needed.

At point 2, a volume of fluid is injected in one end of the sealed cell while an equal volume of endogenous fluids (gas or liquid) is withdrawn. Volumes are carefully assessed, and the chamber is then closed until a second pressure equilibrium is reached. The pressure sensor can be part of the sealed chamber or be part of the external pressure regulatory system.

If the second equilibrium pressure is at a higher pressure than the first, it indicates efficient imbibition with impacts of hysteresis (see point 3). If the second pressure is at an equal pressure to first, it indicates efficient imbibition where fluid volume imbibed by the sample cores is equal to the fluid hydrocarbon released (see 4). If, however, the second pressure is at a lower pressure than first, this indicates low efficiency of imbibition where fluid volumes imbibed by cores is greater than fluid hydrocarbon released or there are impacts of hysteresis (see 5).

In points 6-8, a second experimental fluid is injected, similarly to what was done at 2. The same outcomes (3-5) may then occur. This experiment may continue indefinitely with various fluids, thereby determining wettability, and other rock and fluid features.

FIG. 5A-D show additional variety in sealed high pressure chamber 550 configurations, wherein in each case 510 is an incoming high pressure line, 520 is the incoming high pressure fitting, and 530 is the upper chamber cap. The core sample is 540 and inert fluid is 560. The outgoing high pressure fitting is 570 and the outgoing pressure line is 580.

Figure 5A:
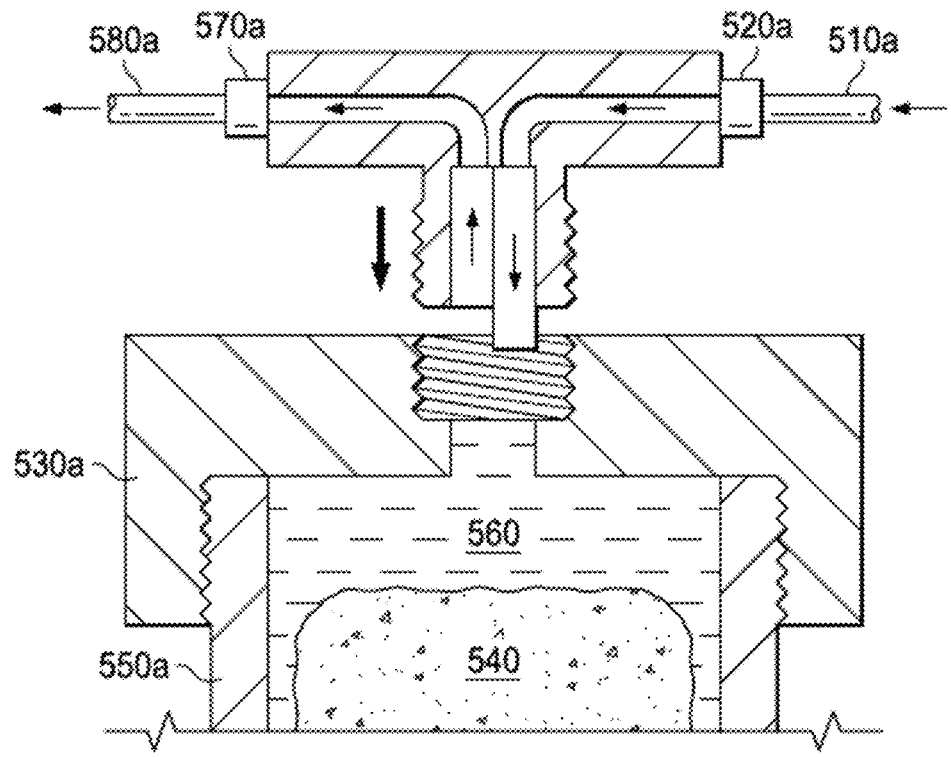
FIG. 5A-D show a variety of configurations of a high pressure sealed cell unit.
Figure 5B:
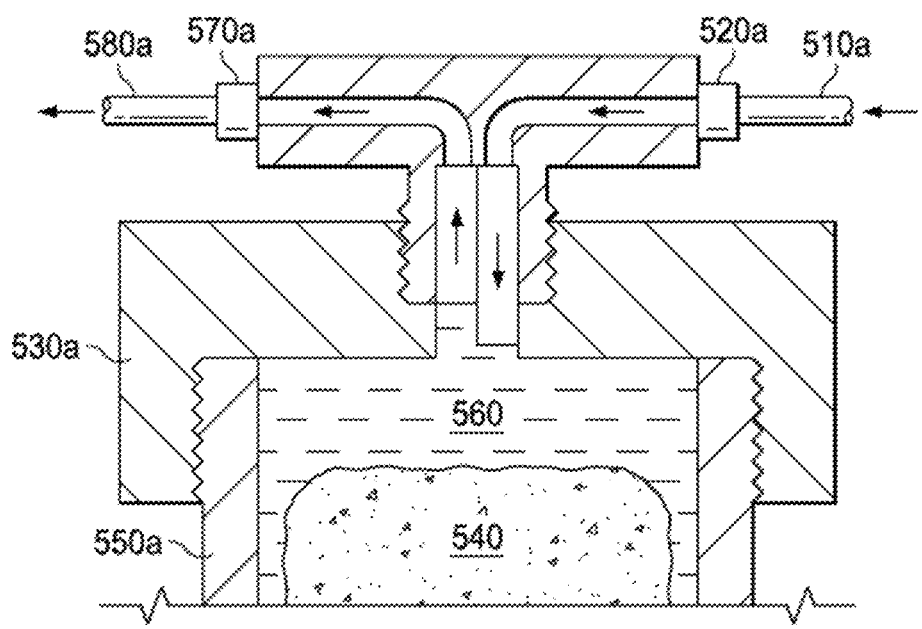
Figure 5C:
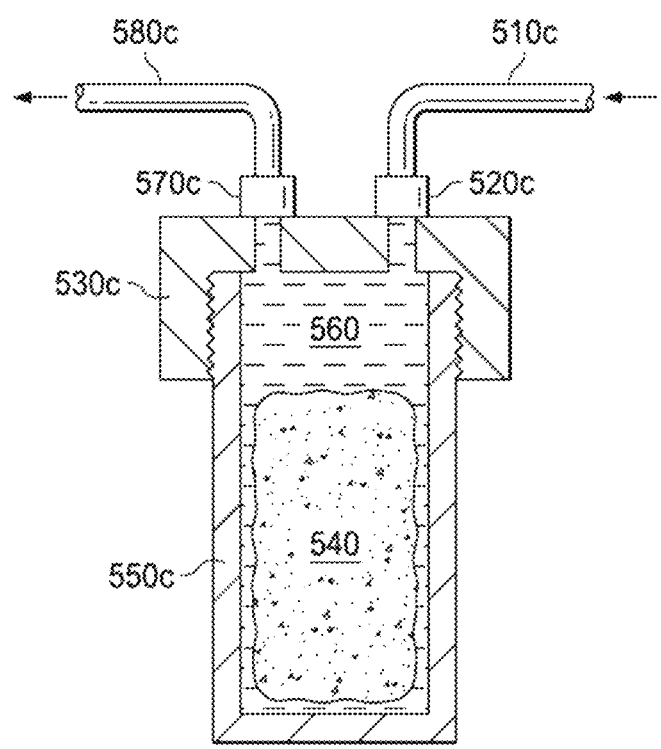
Figure 5D:
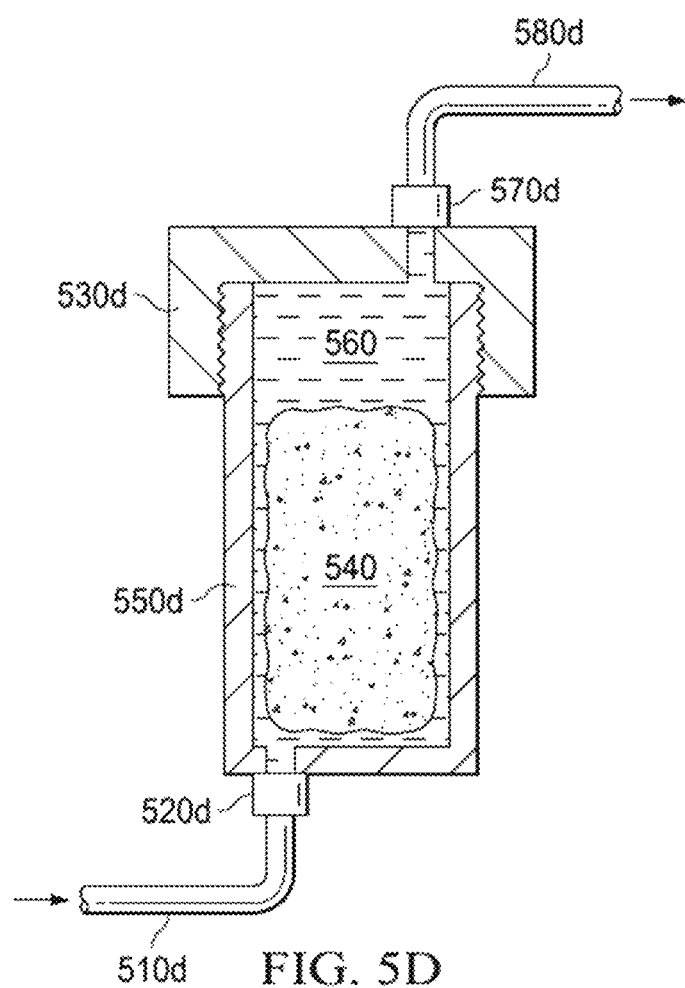

In FIG. 5A, a single split port with and in- and out-flow is shown that threadedly or snap fits into cap 530. It is shown fitted into place in FIG. 5B. FIG. 5C shows a cap 530 with two ports 520, 570. FIG. 5D shows the two ports on opposite ends of the chamber. Although the lower port is on the chamber body or base, FIG. 3A shows ports on both ends, where both ends are capped.

Figure 6A:
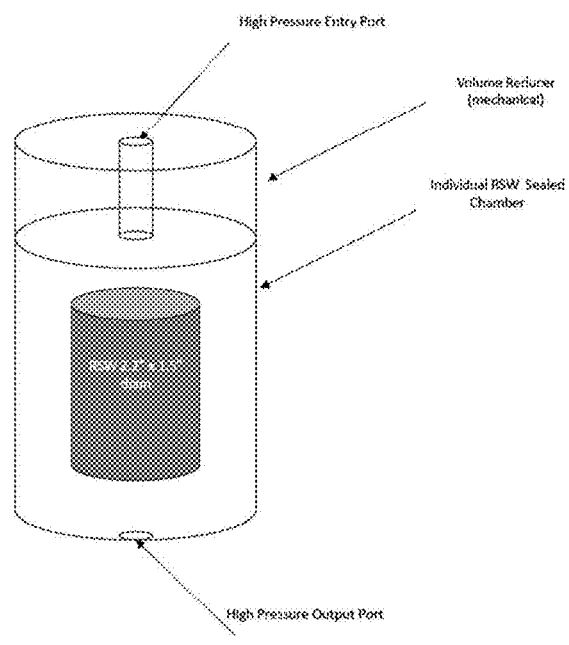
FIG. 6A-B shows two example high pressure core delivery and experimental vessel configurations with two end ports 6A and side and end ports 6B.
Figure 6B:
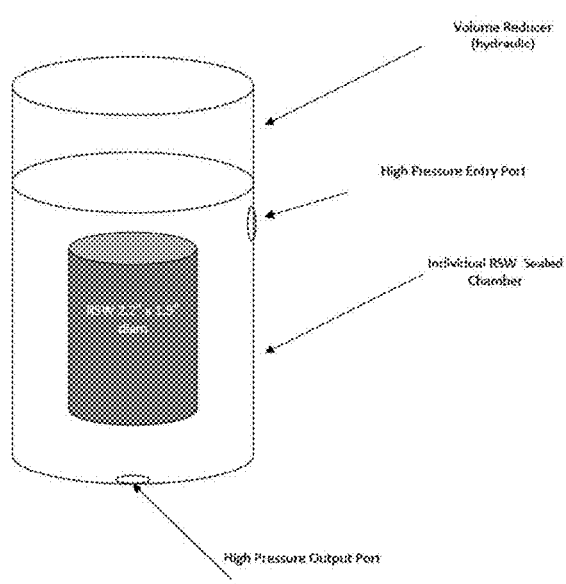

FIG. 6 shows two example high pressure core delivery and experimental vessel configurations, 6A with entry and exit ports on opposite top and bottom ends of the cylindrical core, and in 6B with a side entry port and end exit.

Because the core chamber is to serve both delivery and experimental vessel functions, it may be preferred in some embodiments to make the interior diameter of the inner chamber larger than the diameter of the core sample (see e.g., FIG. 6), thus providing a space for the ingress of experimental fluids. Such can be accommodated by making the interior chamber larger, or by reducing the diameter of the coring bit, or a combination thereof.

Figure 7:
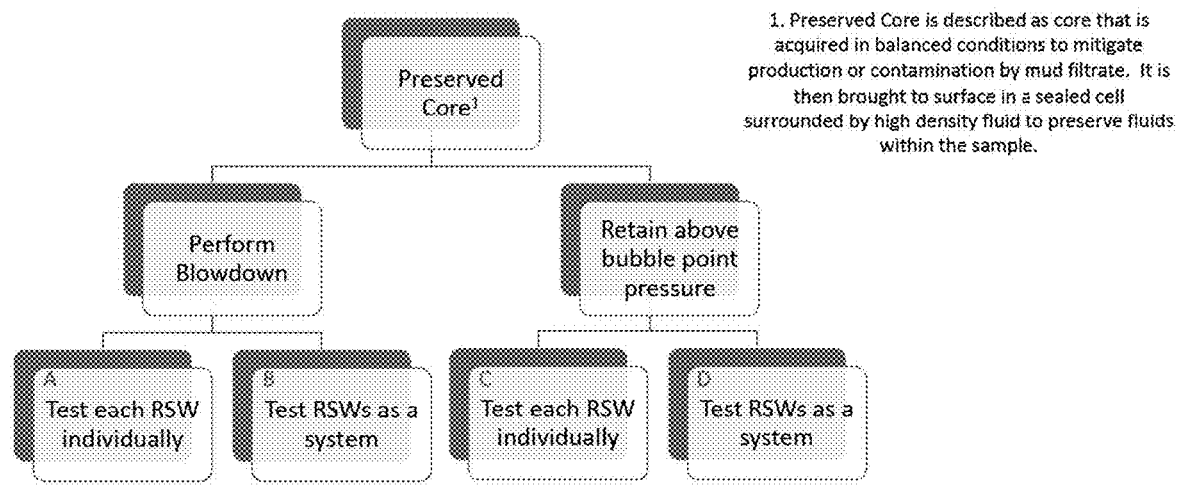
FIG. 7 is a schematic of possible experimental design.

FIG. 7 is a schematic of possible experimental design and which experiments follow which steps.

Coring and Retrieval

In use, the core chamber is assembled inside the corer tool with e.g., the lower end closed and the upper end open, typically with the upper cover near the cover deployment arm (if the core chamber is above the drill bit, then the lower end is open and the upper closed). The system is operably connected to e.g., a wireline and/or drill string and deployed downhole. At the desired interval, a signal is sent to the corer tool, and it deploys the sidewall drilling bit, drills a sample, and places the sample down into the core chamber. This can be repeated a number of times over a small interval.

Once sampling is complete, a signal to the coring tool causes the cover activation mechanism to close the upper end, e.g., by screwing the upper cover into the upper end, providing a pressurized container. Where sensors and heaters are present, this data is collected and as the system is retrieved to the surface, the heater compensates for the drop in temperature with decreased depth. Once on the surface, the system is at least partially dissembled, and the core chamber sent to lab facilities.

Once in the lab, the specialized ports can be used to access the core chamber without loss of P (and in some embodiments T). Fluids can be injected into one end and endogenous fluids collected at the other end either at timed intervals, or continuously or after the system re-equilibrates. Once high pressure tests are complete, the core chamber can be opened and normal ambient pressure experiments can continue with the now fully accessible core samples.

Core Analysis

Core analysis proceeds with all high P or PT tests before removing the core from the high pressure corer chamber and performing cleaning and/or destructive tests. Exemplary tests may include one or more of the following.

Wettability: Wettability is defined as the tendency of one fluid to spread on or adhere to a solid surface in the presence of other immiscible fluids. The importance of wettability has long been recognized as affecting the measurement of special rock properties. Wettability is a major factor controlling the location, flow, and distribution of fluids in rocks. Undoubtedly, in situ wettability is one of the most difficult reservoir parameters to quantify. It is virtually impossible to core a reservoir rock and be certain that it's in situ wetting preference has not been altered. The goal of the core analyst must be to mitigate wettability alteration during core acquisition and sample preparation. It may be possible in some rock types to restore the original wetting preferences of the rock by cleaning, saturation with reservoir fluids, and aging. The most common methods to measure wettability include USBM, Arnott, contact angle (parallel crystal plate) techniques, and variations on these basic methods. The dynamic Wilhelmy plate can be used for measuring the wetting character of oil, brine, and rock systems. This method is simpler and less operator-dependent than standard contact-angle procedures and can be used to examine the effects of contaminants such as drilling-fluid components.

With a HP core chamber now available for use as an experimental vessel, however, the method can be modified to measure in-situ wettability, which can now be preserved at reservoir conditions. Where single phase hydrocarbon conditions exist in the subsurface, this single phase will be preserved thus the non-wetting gas phase has not altered the reservoir wettability conditions. Preserved in-situ wettability allows production simulation to occur at reservoir conditions without the error-prone methods of core restoration. For the first time, wettability alteration by fluid chemistries may be observed at reservoir conditions.

Pore Volume Compressibility Pore-volume-compressibility (PVC) data are used to compute pore-volume reduction during pressure depletion of a reservoir. This variable can play a major role in the prediction of hydrocarbon recovery. The majority of PVC tests conducted by service laboratories are performed under hydrostatic load. An empirical uniaxial correction factor is then applied to hydrostatic data to estimate rock behavior under reservoir stress conditions. These factors assume linear-elastic strain conditions, equal horizontal stresses, the Biot pore-elastic constant equal to one, and a value for Poisson's ratio. Unfortunately, hydrostatic loading rarely reflects in situ stress conditions.

Efforts by experts in rock mechanics and by core analysts have resulted in improved PVC technology. The preferred method of measuring PVC is uniaxial strain (triaxial stress) with pore pressure to approximate in situ conditions. The total vertical stress (overburden) and lateral strain are maintained constant during pore pressure depletion (reservoir pressure drop during production). Stress-path dependence is evaluated and elastic constants are measured directly. Although this approach is more complicated, it is more representative of reservoir conditions than hydrostatic loading. Nevertheless, some authors argue that theoretical corrections to hydrostatic tests are accurate for most reservoir situations. Bulk-compressibility factors critical in subsidence studies as well as in the evaluation of core compaction factors should also be measured triaxially.

With a HP core chamber now available for use as an experimental vessel, however, the method can be modified to perform a variety of studies on core that exists in the same or nearly the same state as it existed in situ. Results from production simulation across a sealed cell will apply differential pressure similar to in situ differential pressures during well production, thus eliminating the effects of pore volume compressibility and the need to correct for these effects via laboratory measurements or models.

Capillary Pressure: Several other techniques besides centrifuge have been used for measuring capillary pressure. These include the porous-plate, mercury-injection, and water-vapor de-sorption methods. Porous plate is the original technique to which all others are referenced. A new method of generating capillary-pressure curves from centrifuged samples uses magnetic-resonance images to obtain fluid saturation distribution in Berea sandstone cores. The development of capillary-pressure instrumentation has far exceeded advancements in theory. Automated mercury-injection instruments can now attain pressures in excess of 60,000 psi. Researchers recently compared different techniques including water vapor desorption for obtaining capillary-pressure data in the low-saturation region. Clearly, differences exist in measurement techniques and each method has its inherent limitations.

With advances in slow constant-rate mercury-injection technology, it is now possible to perform detailed pore-space evaluation beyond the simple calculation of capillary pressure. The recent "APEX" (apparatus for pore examination) porous-media technology resolves pore space into pore bodies (subisons) and pore throats (risons) each of which is characterized by entry pressure and volume. Distribution functions are used to express macroscopic rock properties in terms of pore-scale properties. APEX technology can be used to estimate electrical and flowfimbin properties, measure critical gas saturation and irreducible water saturation, improve petro-physical evaluation, evaluate fluid trapping tendency, and predict formation-plugging potential.

Relative Permeability: Relative permeability is one of the most important reservoir parameters measured in the laboratory. These data are used for prediction of reservoir performance and determination of ultimate fluid recoveries. This information is critical in designing various fluid-injection schemes, evaluating water and gas-coning behavior, examining formation-damage potential, and in the development of pseudo-functions for numerical reservoir simulation. The relative permeability of a rock to each fluid phase can be measured by either steady-state or unsteady-state methods. Under steady-state conditions, a fixed ratio of fluids is forced through the test sample until saturation and pressure equilibria are established. Unsteady-state relative-permeability measurements can be made more rapidly than steady-state measurements; however, the mathematical analysis of unsteady-state data is more difficult and, like centrifuge data, interpretation remains controversial. The unsteady-state technique is an operationally simple test that can be performed by viscous or centrifugal displacement. The unsteady-state technique can be hampered by capillary end effects. These effects can be reduced by injecting fluid at high rates, so that capillary forces become negligible. In many cases flow rates may become impractically high and formation damage can occur. For this reason and others, unsteady-state methods are becoming less desirable for reservoir engineering calculations. Another approach is that the combination of steady-state and unsteady-state methods be used to obtain optimum two-phase flow characteristics. This approach allows the range of relative-permeability information to be extended without increasing the complexity of the steady-state experiment and improves the definition of the relative-permeability curve.

Researchers have placed great emphasis on interpreting relative-permeability behavior in terms of rock and fluid properties. The details of core handling, preservation, drilling fluids and drilling parameters should be known prior to performing relative-permeability tests. Current research is concerned with understanding the effects of fluid saturation, saturation history (hysteresis), wettability, pore-space architecture (especially small-scale heterogeneities), experimental conditions (pressure and temperature), retrograde-condensate flow behavior, and three-phase relative-permeability characteristics.

Electrical Properties: Numerous papers have been published on the measurement and analysis of Archie parameters. The effects of laboratory procedures on the measurement and analysis of the saturation exponent have shown this variable to be one of the most difficult petro-physical variables to quantify. Both MRI and imaging have been used to show fluid-saturation (distribution) problems during the de-saturation phase of the resistivity-index measurement. As de-saturation progresses, the saturation exponent can vary because of non-homogeneous saturation distribution. The impact of petro-physical properties on the observed curvature in log resistivity-index versus log water-saturation plots can be significant.

Dielectric-constant: Dielectric-constant (relative-permittivity) measurement research continues to be of interest with the introduction of several newly developed high frequency dielectric-constant logging tools. Other areas of electrical properties research include the development of laboratory "induction-like" instrumentation. This apparatus will be used to coaxially measure induction parameters at 100 kHz on 4-in. full-diameter core. Another innovative technology uses high-resolution electrical-resistivity imaging of whole and half core to provide a calibration of down-hole electrical imaging logs. The resistivity imaging of core is sensitive to the same fabric and structural detail as down-hole electrical image data and provides a means of converting electrical resistance images into physical properties. Resistivity images are explained in terms of sedimentary fabric and small-scale petro-physical features. Resistivity anisotropy can be examined by directionally constraining electrical current flow.

Geological Testing: The most important geological technologies in rock characterization are:
1) petrography-used in the visualization, description, and systematic classification of rocks and minerals, especially thin-section microscopy and SEM.
2) compositional analysis—a branch of geochemistry that deals with the identification and quantification of minerals (for the purpose of brevity, organic geochemistry and fluid analysis will not be covered).
3) sedimentology—the study of processes by which sedimentary rocks are formed, e.g., diagenetic evaluation, interpretation of depositional environment.

All three technologies are used in the interpretation of basic and special core analyses. Petro-graphic and compositional data are critical in the evaluation of petro-physical, completion, and drilling engineering data, e.g., mineralogy, clay morphology and distribution, rock texture and fabric, and formation-damage potential technique, details of pore in-fills in sandstones, matrix in shales, and fine-scale interlayering of clays is revealed. Image-analysis technology has added exceptional power to CT, MRI, and other tomography methods. Imaging technology can be used to non-destructively examine pore-space rock-frame relationships, determine mineral and fluid type and distribution, and study petro-physical parameters.

Compositional Analysis: Virtually all of the routine methods used to determine the composition of rocks and minerals are semi-quantitative, e.g., X-ray diffraction (XRD), energy and/or wavelength dispersive spectrometers (EDS), polarized-light microscopy, Fourier-transform infrared spectroscopy (FTIR).

Accuracy and precision in the rock and mineral composition laboratory can be a major problem. As with most rock-characterization techniques, the lack of standards for rock preparation, reference materials to ensure consistency among laboratories, and instrument design can lead to discrepancies in compositional results. Laboratory rock and mineral determinations are the standard by which in situ measurements are compared, e.g., nuclear-spectrometry logging tools (geochemical logs). Caution must be exercised when using laboratory-derived mineral and elemental data. Each method must be examined carefully to determine experimental limitations, accuracy and precision in testing, as well as potential mineral alteration processes that can occur when a rock is removed from its environment.

Sedimentology: Sedimentology is a very broad (mostly qualitative) geo-science dealing with the study of sedimentary rocks and the processes by which they are formed. Examination of full-diameter core is useful in determining the depositional environment of a formation and with other data can be used to explain facies relationships. Understanding the genesis of sedimentary structures, textural features, and porosity evolution adds a new dimension to the quantitative assessment of physical properties. Integration of Sedimentology into the rock characterization program adds valuable insight to the design of core preservation methods, core sampling procedures, and laboratory tests.

Once the high P tests are complete, basic (routine) core analysis involves the measurement of the most fundamental rock properties. Porosity (storage capacity for reservoir fluids), permeability (reservoir flow capacity), saturation (fluid type and content), and gross lithology all provide critical information in deciding whether a wellbore will be economic.

Fluid Saturation: Basic core analysis begins with the extraction or cleaning of fluids contained in the pore space of rock. Cleaning may be accomplished by passive Dean-Stark or Soxhlet extraction, solvent-flushing in a pressurized core holder or centrifuge, or gas-driven solvent-extraction. The more time consuming and nondestructive Dean-Stark distillation method provides an accurate measurement of fluid saturation(s) and allows for restored-state testing on the solvent-extracted sample. The summation-of-fluids method, which requires retorting the sample, is still commonly used in the evaluation of percussion sidewall samples. However, this method of obtaining fluid saturations is not used for cleaning. Retorting is destructive and its use in consolidated rocks is dwindling. The Karl Fischer titration technique can be used in many cases to more accurately define water saturation. When the objective of the analysis is to obtain saturation information, X-ray computerized tomography (CT) are alternatives to the time-honored extraction methods. Magnetic-resonance techniques have the advantage of being able to distinguish bound from movable fluid as well as to estimate other critical reservoir parameters, e.g., permeability, wettability. All solvent-extraction techniques affect the rock wettability to some degree and this must be considered when designing special core tests.

Porosity: A number of techniques are employed for the measurement of porosity in consolidated rocks. Boyle's-law helium-expansion is a standard method for measuring either pore volume or grain volume. Bulk-volume measurements are generally determined by fluid displacement (Archimedes principle) or by callipering plug samples. With Boyle's-law and bulk-volume data, bulk and grain densities can be determined by also weighing the sample. These methods are accurate and reproducible if proper operating procedures are followed.

Although significant progress has been made in both CT and MRI to measure the porosity of saturated cores, these instruments are not widely available. Both CT and MRI instruments are expensive and require highly skilled operators, but as the costs continue to decrease, their availability should increase. Tomographic imaging using thermal neutrons is another emerging technology that takes advantage of directly imaging the hydrogen content of samples and thus measures porosity with high sensitivity. A major limitation of this technique is the availability of neutron sources that are not reactor-based. As new, more intense sources are developed, this technique may become practical for basic core analysis.

Permeability: Routine single-phase permeability measurements are fundamental to understanding fluid flow in porous media. Darcy's law is the empirical expression used to explain the relationships among the variables involved in the flow of fluids through rocks. Permeability can be estimated indirectly using wireline logging and pressure transient methods, or directly with core-based techniques. Indirect methods often prove to be unreliable; however, integration of methods at all scales yields the best estimate of reservoir permeability. The nuclear magnetism log measures movable formation fluid and spin-lattice relaxation times. One of the more promising indirect permeability technologies employs spin-echo magnetic-resonance technology. Formation testers, acoustic (Stoneley-wave velocity), and nuclear (geochemical) logging tools are also commonly used to estimate permeability, but core-based permeabilities are considered the standard to which all other measurements are compared.

Direct (core-based) single-phase permeability measurements can be separated into four major categories: those utilizing a flowing gas under steady-state or unsteady-state (transient) conditions, or a flowing liquid under either condition. Most routine permeability measurements are made with gas, e.g., air, nitrogen, or helium. Liquid permeability measurements are more time consuming; however, water permeabilities may provide more realistic data for some formations. Nonetheless, 12 concluded that comparisons of liquid and air permeabilities show a strong correlation supporting the use of air permeabilities in evaluating reservoir quality.

The use of unsteady-state single-phase gas permeability technology has increased since the mid 1980's. Porosity, air permeability, equivalent nonreactive liquid permeability (Kiinkenberg gas slippage), and Forcheimer (inertial) factors can be measured at overburden conditions in a single automated experiment. These data are useful in reservoir-engineering calculations and can be acquired quickly, even in low-permeability rocks.

Significant progress has been made in developing instrumentation to perform probe (mini permeameter) permeability measurements. Recent interest in small-scale reservoir heterogeneities, reservoir characterization, and outcrop evaluation has revitalized this technology. The probe permeameter has the advantage of making localized, nondestructive, and rapid measurements of permeability with a high resolution at a low cost. Permeability distribution may be examined in heterogeneous formations and explained in terms of depositional environment and diagenetic controls without cutting core plugs.

Probe-permeameter measurements are performed by injecting compressed nitrogen or air through a small diameter injection tip, which is pressed against a rock surface. A rubber seal is used to prevent gas leakage past the probe. If the gas-flow geometry is known, permeability can be calculated from flow-rate and pressure measurements using an appropriate form of Darcy's law. Both steady-state and unsteady-state versions of the probe permeameter are in use. Unless the rock is an isotropic, homogeneous porous media, gas flow around the probe tip must be represented by an empirically derived geometric factor. The flow model is then tested and calibrated with core plugs of known permeability. Some have taken this technology one step further with the introduction of an automated laboratory-probe permeameter. As with all gas-permeability measurements, slippage and turbulence factors, rock saturation state, and equipment limitations must be taken into account in evaluating data quality. Because of the vast number of probe-permeability measurements possible on core and outcrops, one of the greatest challenges will be the statistical treatment of these data.

Sealed Cell Hydrocarbon Production Experiments

Currently available methods for designing and testing chemistries to alter properties in tight reservoirs introduce significant uncertainty. Ambiguities or errors in measurement arise from mud column and atmospheric exposure, altered or non-representative pore surface and pore throat characteristics, and non-representative temperature and pressure regimes. A high pressure core chamber, such as CoreVault®, modified as described herein and laboratory procedures for its use may provide a novel testing environment to reduce or eliminate the aforementioned uncertainties. If successful, this experiment would verify a means to rapidly test multiple IOR fluids at relatively low cost. This information could result in rapid development of chemistries that could theoretically increase hydrocarbon production from unconventional reservoirs by more than 20%.

1) Dual valve high pressure core chamber provides a representative in-situ reservoir sample (rock+fluids) inside a vessel that allows for identifying the in-situ or native wettability state of the reservoir, wettability alteration and relative permeability studies to be conducted.

2) Incremental hydrocarbon production when replacing FC40 (an inert exclusion fluid) with water or brine, completion fluid, treatment fluid, surfactant, and other well fluid treatments can be measured and those samples analyzed. This can be measured incrementally by first replacing the FC40 with an aqueous solution such as water. Next determine if hydrocarbon is produced in the presence of a designed completion chemistry for wettability alteration. Note the differences in produced fluid compositions based on fluid-rock interactions, first with aqueous solution and secondly with completion fluid. Determine changes in bubble point as it is altered by wettability of different fluids.

Once we establish more water or oil wet (initial condition), subsequent tests may be used (even on samples immediately transferred from the vessel) to understand what we want to alter. We may also get an idea of imbibition extent/rate in the vessel, and once the baseline wettability is established, we may test what subsequent aqueous fluid to flush next to e.g., encourage imbibition and/or mitigate capillary trapping of the non-wetting phase, etc.

3) Pressure build-up data may be collected after sealing the blown-down core chamber indicating fluid movement from matrix to free space. Rate and type of fluid production can be used to determine the nature of pore size from which the hydrocarbon is being produced. It may also be important to keeping the samples at reservoir temperature to keep wax crystallization from occurring (which lines pores, affecting wettability towards more oil wet).

4) Finally, we can develop a gas transient model (GTM) to describe the pressure-volume relationship between gas and porosity. This might be similar to gas filled porosity GTM models for NMR. Pressure/volume and gas origin may be calibrated to determine gas dissolved into dead oil versus gas entering free pore space. Ancillary techniques, such as SEM, may be used to help calibrate the results.

Proposed Experiment Using an Existing HP Core Chamber

Since a prototype dual valve core chamber has not yet been built, our initial experiments will proceed with a commercially available sealed cell core sampling device, such as the CoreVault® device available from Halliburton. The device has been modified however, to provide chamber access at reservoir temperature and pressure by connecting a high pressure split port with an inflow and outflow (see FIG. 5A).

Two CoreVault® samples will be collected from a well characterized reservoir, where the uncertainty of expected hydrocarbons in place is relatively low. We will sample approximately 10 foot intervals based on either a Triple Combo or Quad Combo Wireline Log as well as a downhole wireline NMR to ensure homogeneity. These samples are identified as CV1 and CV2 herein.

A "Triple Combo" wireline log is GEM-CSNG-WavesonicX-Y Dipole which provides measurements of gamma ray, density, porosity, resistivity, caliper, and temperature as described in Zhao (2015). A "Quad Combo" such as described in Truax (2011) also has GEM-CSNG-WavesonicX-Y Dipole, but adds a rotated dipole sonic log. The triple or quad combo log is run to ensure core samples are extracted from an area with high total organic content (TOC). Passey's (1990) provides one method of TOC calculation with well log data. These are common logs used in the industry and are only used to identify key targets for sidewall core samples.

1. Conduct a bubble point experiment (Clark, 2009) to determine an actual bubblepoint by maintaining reservoir conditions with the sealed cell core sample chamber. By monitoring the pressure or volume in the chamber, we can observe changes in the chamber either showing the release of gases or the release of hydrocarbon. As a first step, the sample at reservoir temperature and pressure is exchanged from the inert fluid to a aqueous completion fluid. Once the fluid volume is exchanged, pressure is monitored over time to observe the overall loss or gain of fluids in the pore space. If pressure increases, that indicates that hydrocarbons are being liberated from the pore space. If pressure decreases, that indicates that aqueous solution is being taken up by the sample. Because the core sample has been maintained at reservoir pressure, fewer gases will have been released from the sample, additionally hydrocarbons will still be in their natural state within the pores. This is the opposite of standard core samples where hydrocarbons, water, and gases are forced out, sometimes violently, by the large drop in pressure.

2. Perform blow down and shut in for a pressure build up experiment.

3. Subsample minimum gas volume for adequate composition and isotopes. Liquid hydrocarbon is not expected, but if produced, spin off inert fluid, subsample and return to the core chamber.

4. Remove inert fluid from core chamber and measure the volume of inert fluid. Sample the inert fluid to determine its composition before and after exposure to core sample. Process of removal should be designed to minimize atmospheric exposure of the rock samples. This could be iterations of inversion of the canister to extrude used inert fluid with uncontaminated inert fluid, use of non-miscible gas (He) or use of lower density fluid such as water to begin the next phase of the experiment.

Water Imbibition & Incremental Production with CV1

5. Replace inert fluid volume with aqueous fluid.

In one approach, to control which sample is imbibing water, a stepped volume injection could be programmed to expose 1 rock sample at a time. The vessel could then be shut in to monitor incremental production from each individual sample.

In another possible approach, we can treat the entire volume at once, which may require subsequent volumes of water to be introduced. Shutting the vessel in and monitoring any pressure changes over time may indicate the efficiency of the material to imbibe water at atmospheric conditions. We may also broaden this procedure to perform it prior to blow down at reservoir conditions, or any PT conditions for that matter, with a method of controlled input and output of volumes from the sealed cell.

6. Seal canister and recombine the produced gas (minus any subsampled gas) to return the core sample back to reservoir conditions with gas volume, hydrocarbon and any other produced fluid. Reconstituting the original reservoir prior to additional testing may provide the most direct look at the in-situ reservoir to date. Monitor the pressure response to the volume of gas injected for use in a potential Gas Transient Model (GTM).

7. Place the core chamber in a temperature chamber and bring the sample back to reservoir conditions.

8. Allow adequate soak time (e.g. 2-10 or 5 days) and begin a bubble point experiment based as previously described only this time the sample will have original gas, fluids, temperature and pressure. Determine Instantaneous Shut In Pressure (ISIP) of chamber after bubble point experiment. Compare to previous ISIP after water and gas injection. Determine change in pressure after reconstitution and compare to initial ISIP from inert fluid.

9. Repeat steps 2 & 3 above.

10. Remove free fluids from the core chamber and measure volumes and subsample for desired identification or further experimentation.

Completion Fluid Imbibition & Incremental Production with a Core Sample

In another embodiment, the chamber may be reconstituted and subsequent fluids tested. Although each subsequent test will alter the core slightly from its original state, the overall change will help identify those solutions that achieve better properties and determine what the optimum solution will be for the given reservoir.

If material transfer between apparati is involved, we may consider freezing the samples core to minimize additional losses. This may cause some pore structure damage where there is water.

11. Replace water volume with designed wettability alteration completion fluid using method similar to step 4, above.

12. Seal the core chamber canister and recombine produced gas and liquid (minus subsampled hydrocarbons) using method similar to 6.

13. Repeat steps 7-9.

14. Remove completion fluid from the core chamber and measure the volume of the completion fluid.

Repeat with subsequent fluids until the desired fluid properties are achieved. Ideally the fluid would be inexpensive and exchange rapidly with the hydrocarbons in place to liberate oil at a better rate than untested completion fluids.

15. Proceed with rotary side wall processing (MICP, SEM etc. crucial for verification of porosity).

Standard Experiment with Core Sample 2

1. Conduct a bubble point experiment on CV2 sample based on SOP, as previously described.

2. Perform blow down and shut in for pressure build up experiment as previously described.

3. Subsample minimum gas volume for adequate composition and isotopes.

4. Remove inert fluid from the core chamber and measure the volume of inert fluid.

5. Remove rotary side wall cores from the core chamber and conduct Dual Energy CT and NMR, making every attempt to preserve core and avoid atmospheric exposure. Target pore size range may be calculated through a combination of computed tomography (CT), Scanning Electron Microscopy (SEM), and Nuclear Magnetic Resonance (NMR) technologies. Dependent upon the sample and computed pore size, one or two of the above methods may be used to assess pore size in a sample. In one embodiment NMR is used to determine the pore size range from which the oil is produced. In another embodiment, CT technology is utilized to monitor the movement of the fluids inside the cores. CT can also be used to validate the NMR results, which revealed a direct relation between CT imaging and NMR results.

Water Imbibition and Incremental Production with CV2

6. Place the 10 rotary sidewall (RSW) core samples in separate low-volume testing vessels, similar to individual core desorb chambers, thus allowing for 10 distinct fluids to be tested on the preserved core samples.

7. Place the desorb chambers in a temperature chamber and bring the samples back to reservoir conditions.

8. Allow adequate soak time (5 days, but may vary dependent upon reservoir conditions and gas uptake) and begin the bubble point experiments, as previously described.

9. Follow steps 2 & 3 above for each individual chamber.

10. Remove and subsample water for spin-off.

11. Conduct NMR while making every attempt to avoid atmospheric exposure.

Expected Dataset Provided

Volumes and compositions of incrementally produced hydrocarbons produced from matrix in the presence of varying wettability altering fluids. By sampling multiple RSW samples under various conditions, a comparison matrix can be created to identify the best solutions for completion and/or reservoir treatment.

If the samples are maintained in a sealed chamber, later experiments may be conducted to determine if the core samples still have similar properties to the original samples, and the samples may be treated with various solutions to develop an additional treatment matrix, this one outlining EOR properties that achieve favorable hydrocarbon displacement and reservoir wettability characteristics.

Maintaining the samples in a controlled manner to limit exposure of the core sample to atmosphere increases the likelihood of being able to recreate reservoir conditions at a later date.

NMR measurements can be done on as-received samples and after each subsequent wettability alteration. Ideally, a clear 4-D signal of wettability alteration (reduction in residual oil, increase in irreducible water) will be developed over time. Changes in bubble point, hydrocarbon content, and treatment fluid can then be monitored in subsequent experiments and modeled over time.

Pressure build up during shut in periods after blow down experiment.

GTM-like data for gas filled porosity. Ideally, subsequent sealed cell experiments would establish a trend of produced liquids and gas that would supplement the 4D signal from NMR data further building evidence of pore scale hydrocarbon production. Alternatively, the efficiency of recombining gas and liquids to a single phase at reservoir conditions and reoccupation of pore space may be the result of the measurement. This trend could in of itself provide insight.

Post Blowdown Assays

Using the herein described core chamber (aka primary vessel), we can test the effect of various stimulation fluids on production, according to the following protocols.

Conduct a blowdown experiment according to standard operating procedures, while maintaining the temperature of vessel.

Isolate liquid and gas hydrocarbon volumes for reintroduction to the core chamber.

Subsample and record [minimum] volumes.

Place gas and liquid volumes (hydrocarbon and inert fluid) in an external vessel with pump. Replace subsampled volumes with additional inert fluid to maintain a constant volume.

Attach a secondary vessel to the primary testing core chamber.

Stepwise increase temperature of hydrocarbons and inert fluid volume back to reservoir temperature at 10° C./hour. Increase pressure on pump to reservoir pressure at <500 psi/hour to avoid forced imbibition.

Once near reservoir conditions, pump additional inert fluid volume equal to dead space volume into the secondary vessel to push all produced fluids back into the primary core chamber, which is then resealed.

Maintain primary core chamber at downhole conditions for 24 hours, monitoring both internal and external temperature and pressure conditions Using test fluid 1, ideally of lower density than the inert fluid, heated to temperature and at pressure conditions of the sealed vessel, begin the staged introduction across the cores at a surrounding fluid volume equal to the length (~2.25" but exact recording of length measured during collection) of each individual core sample. The staged flooding would be equal to ~35 cc of fluid around each core of ~65 cc. Rate of flooding is conducted at 35 cc/hour and followed by shut-in of the vessel for 24 hours to reequilibrate after each individual core is subjected to the test fluid. As test fluid 1 is introduced through valve 1, inert fluid, void of hydrocarbons at native conditions, exits through valve 2 in order to maintain constant volume and pressure. Egressed fluids can be measured for volume and assayed for chemical content.

Each stage of introduction will be monitored during the shut-in period for vessel internal pressure deviations which will be used to adjust volumes calculated to ensure adequate volume in—volume out.

After all inert fluid is replaced with test fluid 1, a final shut-in of one week is conducted at reservoir conditions.

A second blowdown experiment according to standard operating procedures (SOP) is conducted.

Isolate liquid and gas hydrocarbon volumes for reintroduction to pressure vessel.

Subsample and record [minimum] volume

In one iteration, conduct the aforementioned experimental procedure on additional fluids or gas to simulate secondary and tertiary recovery methods.

In another iteration, continue to individual core sample testing methodologies.

Conduct NMR T1-T2 2D mapping on all individual samples according to SOP.—Use produced gas as an accurate gas filled porosity measure and make every attempt to preserve core and avoid atmospheric exposure through container and temperature methods.

Conduct gas chromatography from C1-C8+, isomers and isotopes on all subsamples. Use cryo-enrichment methodologies when necessary.

Conduct Dual Energy CT and standard rotary side wall core processing beginning with non-destructive experimentation.

The above methodology within the described vessel permutations provides us with the capability of interpreting molecular production from a reservoir at accuracies far surpassing all existing technologies. In addition, rapid prototyping of completion fluid chemistry for maximum production drive at near virgin reservoir conditions would be possible for the first time. Further, in-situ wettability conditions could be interpreted prior to artifacts such as long-chain hydrocarbon crystallization permanently impacting those measurements.

Preblowdown Assays

The above assays are done after blowdown, but with the new core chamber, we can do pre-blowdown assays as well. An exemplary methodology is provided.

Place the sealed core vessel/chamber with two ports in a temperature-controlled environment with capabilities of heating to reservoir conditions. Fill the secondary vessel with test fluid 1 ideally of lower density than the inert fluid used in the core vessel. Use volume of test fluid 1 of equal volume to the inert fluid volume in the core vessel, plus any additional volume to account for dead space in the secondary vessel and attachment apparatus.

Fill the secondary vessel at volume and pressure conditions at laboratory temperature equating to expected pressure conditions of the sealed vessels at reservoir temperature.

Connect the secondary vessel to the primary core vessel at highest point with an initially closed metered valve. Connect a tertiary capture vessel with a metered valve and variable volume pumping capabilities at high temperature and pressures (a high pressure syringe) to the lowest core vessel port. Initial volume is equal to the helium vacuumed dead space.

With vessels in the temperature controlled environment, step the temperature to the reservoir temperature at 10° C./hour. Maintain the vessels at reservoir temperature and thus the core vessel and secondary vessel at reservoir pressure for 24 hours.

To begin the staged introduction across the cores at a surrounding fluid volume equal to the length (~2.25" but exact recording of length measured during collection) of each individual core sample, open valve between secondary vessel and core vessel. Then open the valve between the core vessel and the tertiary capture vessel.

Use metered volume expansion in the tertiary capture vessel equal to the inert fluid volume around each individual core. Staged introduction of test fluid 1 should equal to ~35 cc of fluid around each core of ~65 cc. Rate of flooding is conducted at ~35 cc/hour and followed by shut-in of the vessel for 24 hours to re-equilibrate after each individual core is subjected to the test fluid. As test fluid 1 is introduced through valve 1, inert fluid exits through valve 2 to maintain constant volume and pressure inside the core vessel.

During each shut-in period, pressure changes are monitored.

Ideally, at this point in the experiment, we would have the ability to attach different vessels at the entry and exit ports, still without going to blowdown. We could then switch the tertiary capture vessel with a new clean vessel for the expected production phase.

After completing replacement of inert fluid with test fluid 1, shut-in for 48 hours.

Proceed to production simulation phase across core vessel. Using a clean tertiary capture vessel heated to reservoir temperature, begin staged pressure drops across the primary core vessel. Increase the volume of the tertiary capture vessel from 0 (+Helium filled dead space volume) to a volume consistent with initial pressure differential during production (for example 300 psia).

Increase the pressure differential in steps to simulate choke size increases and subsequent drops in flowing bottom hole pressure. In one iteration, continue to increase volume stepwise to blowdown conditions and sample all produced fluids in the single tertiary capture vessel. In another iteration, use new capture vessels for each or selected significant differential pressure steps.

Once the primary core vessel reaches atmospheric pressure, shut-in and reduce temperature to laboratory conditions at 10° C./hr.

Move to specialty and standard core and fluid analysis, such as:

Centrifuge separate all collected fluids. Subsample all gas volume as headspace gas.

Conduct gas chromatography from C1-C8+, isomers and isotopes on all subsamples. Use cryo-enrichment methodologies when necessary.

Conduct GC-MS

Conduct NMR T1-T2 2D mapping on all individual samples according to SOP. Use produced gas as an accurate gas filled porosity measure and make every attempt to preserve the cores and avoid atmospheric exposure.

Conduct Dual Energy CT and standard rotary side wall core processing, beginning with non-destructive experimentation.

This methodology would provide production simulation from preserved core with the ability to quantify and characterize production of native fluids from the host reservoir in the laboratory. Further, controlled exposure of the produced reservoir to test fluids (all possible completion fluid chemistries) could be simulated. This far exceeds any existing capabilities all of which introduce numerous assumptions and uncertainties.

REFERENCES

Each of the following is incorporated by reference in its entirety for all purposes.

Kenyon, W. E. 1997. Petrophysical Principles of Applications of NMR Logging. The Log Analyst 38 (2): 21-43.

Murphy, D. P. 1995. NMR logging and core analysis—simplified. World Oil 216 (4): 65-70. OSTI ID 39931.

Woessner, D. E. 2001. The early days of NMR in the Southwest. Concepts in Magnetic Resonance 13 (2): 77-102.

Dunn, K.-J., Bergman, D. J., and LaTorraca, G. A. ed. 2002. Nuclear Magnetic Resonance-Petrophysical and Logging Applications, Vol. 32. New York: Handbook of Geophysical Exploration: Seismic Exploration, Pergamon Press.

Zhao, T., et al., (2015). "TOC Estimation in the Barnett Shale From Triple Combo Logs Using Support Vector Machine." Society of Exploration Geophysicists, SEG-2015-5922788

Truax, J. A., Galford, J. E., Moake, G. L., Torres, D. O., Cherry, R. E., Mandal, B., . . . Quintero, A. (2011, January 1). Performance of a New 2.35-inch Wireline or Memory Quad Combo for Through-Bit or Small-Hole Logging. Society of Petroleum Engineers. SPE-147400-MS Clark, A. J. (2009). Determination of Recovery Factor in the Bakken Formation, Mountrail County, ND. Society of Petroleum Engineers, SPE-133719-STU.

Alhashim, H. W., et al (2019). Investigation of the Effect of Pore Size Distribution on the Produced Oil from Surfactant-Assisted Spontaneous Imbibition in ULRs. Society of Petroleum Engineers. SPE-195931-MS GB2184835 A method and apparatus for preserving core samples GB2293653 Method And Apparatus For Acoustic Determination Of Porosity

ID201709674 METODE PENENTUAN TEKANAN PEMBENTUKAN GAS KEDAP

US20140090835 Systems And Methods For The Determination Of Gas Permeability

US20180148988 Sealed Core Storage And Testing Device For A Downhole Tool

US20180245415 System And Method For A Pressure Compensated Core

US20180292477 Analyzing Fluids In Core Samples Contained In Pressurized NMR Core Holders With 1 h And 19f NMR US20180371904 Fluid Saturated Formation Core Sampling Tool U.S. Pat. No. 3,986,555 Apparatus for Providing a Packaged Core U.S. Pat. No. 4,230,192 Core Sampling Apparatus and Method U.S. Pat. No. 4,256,192 Apparatus and Method for the Automatic Porosity and Permeability Testing of Multiple Core Samples U.S. Pat. No. 4,258,803 Core Barrel for Obtaining and Retrieving Subterranean Formation Samples U.S. Pat. No. 4,573,342 Apparatus and Method for The Automatic Porosity and Permeability Testing Of Multiple Core Samples
U.S. Pat. No. 4,649,737 Apparatus and Method for Automatic Testing of Core Samples
U.S. Pat. No. 4,702,168 Sidewall core gun
U.S. Pat. No. 4,950,844 Method and Apparatus for Obtaining a Core Sample at Ambient Pressure
U.S. Pat. No. 5,193,059 Method for Identifying and Characterizing Hydraulic Units of Saturated Porous Media: Tri-Kappa Zoning Process
U.S. Pat. No. 5,263,360 Low Permeability Subterranean Formation Testing Methods and Apparatus
U.S. Pat. No. 5,265,462 Method and Apparatus for Determining Permeability, Diffusivity, Porosity, and Gas Storage in Gas-Containing Substrates
U.S. Pat. No. 5,297,420 Apparatus and Method for Measuring Relative Permeability and Capillary Pressure Of Porous Rock
U.S. Pat. No. 5,359,194 X-Ray CT Measurement of Secondary (Vugular) Porosity in Reservoir Core Material
U.S. Pat. No. 5,741,959 Portable Tester for Determining Gas Content Within A Core Sample
U.S. Pat. No. 7,347,284 Apparatus and method for hard rock sidewall coring of a borehole
U.S. Pat. No. 7,600,580 Sealed Core Sample Barrel
U.S. Pat. No. 8,122,976 Valve, Core Sampling Apparatus and Method
U.S. Pat. No. 8,230,946 Apparatus and methods for sidewall percussion coring using a voltage activated igniter
U.S. Pat. No. 8,256,282 In Situ Determination of Critical Desorption Pressures
U.S. Pat. No. 8,307,704 Apparatus and Methods for Gas Volume Retained Coring
U.S. Pat. No. 8,356,510 Formation Core Sample Holder Assembly and Testing Method
U.S. Pat. No. 8,453,766 Hydrocarbon Formation Core Protection and Transportation Apparatus
U.S. Pat. No. 8,621,920 Obtaining and Evaluating Downhole Samples with a Coring Tool
U.S. Pat. No. 9,051,804 Sealed Core
U.S. Pat. No. 9,243,466 Determining Methane Content of a Bottom Sample
U.S. Pat. No. 9,291,541 Apparatus and Method of Measuring Porosity and Permeability of Dioxide Carbon Underground Storage Medium
U.S. Pat. No. 9,376,879 Core Sampling Apparatus and Container Transfer Apparatus
U.S. Pat. No. 9,506,307 High Pressure Coring Assembly and Method
U.S. Pat. No. 9,745,811 Activation Modules for Obstructing Entrances to Inner Barrels of Coring Tools And Related Coring Tools And Methods
U.S. Pat. No. 9,828,820 Methods And Apparatus For Collecting And Preserving Core Samples From A Reservoir
U.S. Pat. No. 9,874,063 & US2014367086 Apparatus And Method For Storing Core Samples At High Pressure
U.S. Pat. No. 9,926,756 Pressure Compensation Modules For Coring Tools, Coring Tools Including Pressure Compensation Modules, And Related Methods
U.S. Pat. No. 9,951,574 Cleaning And Separating Fluid And Debris From Core Samples And Coring Systems
U.S. Ser. No. 10/047,580 Transverse Sidewall Coring
U.S. Ser. No. 10/174,613 Effective porosity determination for tight gas formations
U.S. Ser. No. 10/221,684 Determining Core Sample Volume Within A Sealed Pressure Vessel
U.S. Ser. No. 10/260,300 Measuring Formation Porosity And Permeability
U.S. Ser. No. 10/301,936 Tight gas formation pressure determination method
U.S. Ser. No. 10/301,936 Tight Gas Formation Pressure Determination Method
U.S. Ser. No. 10/317,351 Pressurized NMR Core Analyzer
WO2019070252 Applying Triaxial Stresses To A Core Sample During Perforation And Flow Testing.

We claim:

1. A method of determining wettability of a core sample, said method comprising:
 a) collecting a core sample from a reservoir in a high pressure chamber operably equipped with a pressure sensor, a temperature sensor, a heater, a first high pressure access port at a first end and a second high pressure access port at a second end, said high pressure chamber maintaining said core sample in an inert fluid at reservoir pressure and temperature;
 b) injecting a first test fluid into said first access port and collecting said inert fluid at said second access port without exposing said high pressure chamber to ambient pressure or temperature;
 c) measuring a first change in pressure within the chamber over time; and
 d) determining wettability from a measured change in pressure.

2. The method of claim 1, further comprising repeating steps b-d with a second or more additional test fluids by:)
 injecting a second test fluid into said first access port and collecting fluid at said second access port without exposing said high pressure chamber to ambient pressure or temperature;
 ii) measuring a second change in pressure within the chamber over time; and
 iii) determining wettability from said second measured change in pressure.

3. The method of claim 1, wherein step c measuring occurs after pressure has reached an equilibrium.

4. The method of claim 1, wherein said first test fluid is a brine.

5. The method of claim 1, wherein said first test fluid is a stimulation fluid.

6. The method of claim 1, comprising injecting a second test fluid into said access port without exposing said high pressure chamber to ambient pressure or temperature and collecting said first test fluid at said second access port and measuring a second change in pressure within the chamber over time.

7. The method of claim 6, wherein said second test fluid is a stimulation fluid.

8. The method of claim 1, further comprising a subsequent step of removing said core sample from said high pressure core chamber and assaying one or more characteristics of said core sample.

9. The method of claim 1, further comprising a subsequent step of removing said core sample from said high pressure core chamber and measuring low-field NMR of said core sample.

10. The method of claim 1, further comprising a subsequent step of measuring low-field NMR of any fluids egressing from said core sample.

* * * * *

UNITED STATES PATENT AND TRADEMARK OFFICE
CERTIFICATE OF CORRECTION

PATENT NO. : 11,965,872 B2
APPLICATION NO. : 17/348883
DATED : April 23, 2024
INVENTOR(S) : Martin C. Krueger et al.

It is certified that error appears in the above-identified patent and that said Letters Patent is hereby corrected as shown below:

In the Claims

On Column 24, Line 37, of Claim 2:
"steps b-d with a second or more additional test fluids by:)"
Should read as:
--- steps b-d with a second or more additional test fluids by: ---

On Column 24, Line 38, of Claim 2:
"injecting a second test fluid into said first access port and"
Should read as:
--- i) injecting a second test fluid into said first access port and ---

Signed and Sealed this
Fourth Day of June, 2024

Katherine Kelly Vidal
*Director of the United States Patent and Trademark Office*